United States Patent
Aramaki et al.

(10) Patent No.: US 8,304,283 B2
(45) Date of Patent: Nov. 6, 2012

(54) METHOD FOR PRODUCING ORGANIC ELECTRONIC DEVICE INCLUDING CONVERTING A PRECURSOR FOR A SEMICONDUCTOR LAYER

(75) Inventors: Shinji Aramaki, Yokohama (JP); Noboru Ono, Matsuyama (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 12/577,864

(22) Filed: Oct. 13, 2009

(65) Prior Publication Data

US 2010/0029041 A1 Feb. 4, 2010

Related U.S. Application Data

(62) Division of application No. 11/671,085, filed on Feb. 5, 2007, now abandoned, which is a division of application No. 10/396,512, filed on Mar. 26, 2003, now Pat. No. 7,193,237.

(30) Foreign Application Priority Data

Mar. 27, 2002 (JP) ................................. 2002-089425
Apr. 8, 2002 (JP) ................................. 2002-104639

(51) Int. Cl.
*H01L 51/40* (2006.01)

(52) U.S. Cl. ............ 438/99; 438/149; 438/161; 257/40; 257/642; 257/759

(58) Field of Classification Search ................ 257/40, 257/E39.007, 642, 643, 759, 758, 57; 438/99, 438/149, 151, 158, 161, 197
See application file for complete search history.

(56) References Cited

U.S. PATENT DOCUMENTS

| | | | |
|---|---|---|---|
| 5,284,647 A | 2/1994 | Niedballa et al. | |
| 5,347,144 A | 9/1994 | Garnier et al. | |
| 5,851,930 A | 12/1998 | Bessey et al. | |
| 5,946,551 A * | 8/1999 | Dimitrakopoulos et al. | ... 438/99 |
| 5,981,970 A * | 11/1999 | Dimitrakopoulos et al. | ... 257/40 |
| 6,251,367 B1 | 6/2001 | Platzek et al. | |
| 6,335,539 B1 * | 1/2002 | Dimitrakopoulos et al. | ... 257/40 |
| 6,905,784 B2 * | 6/2005 | Seo | ... 428/690 |
| 2002/0109136 A1 | 8/2002 | Seo et al. | |
| 2003/0067005 A1 * | 4/2003 | De Leeuw et al. | ... 257/72 |
| 2003/0111670 A1 | 6/2003 | Misra et al. | |

(Continued)

FOREIGN PATENT DOCUMENTS

JP 1-173758 7/1989

(Continued)

OTHER PUBLICATIONS

S Kowarik, A Gerlach and F Schreiber, Organic molecular beam deposition: fundamentals, growth dynamics, and in situ studies, Apr. 17, 2008, 1-26.*

(Continued)

*Primary Examiner* — Michelle Mandala
*Assistant Examiner* — Thanh Y Tran
(74) *Attorney, Agent, or Firm* — Oblon, Spivak, McClelland, Maier & Neustadt, L.L.P.

(57) ABSTRACT

An organic semiconductor material comprising a compound which has a generalized porphyrin skeleton and which has a molecular structure such that the distance from the generalized porphyrin ring plane to the center of each atom forming the generalized porphyrin skeleton, is not more than 1A.

8 Claims, 8 Drawing Sheets

U.S. PATENT DOCUMENTS

2003/0203888 A1    10/2003    Boyle et al.

FOREIGN PATENT DOCUMENTS

| | | |
|---|---|---|
| JP | 1-189956 | 7/1989 |
| JP | 1-207975 | 8/1989 |
| JP | 61-202489 | 9/1989 |
| JP | 3-255669 | 11/1991 |
| JP | 5-110069 | 4/1993 |
| JP | 5-152560 | 6/1993 |
| JP | 8-85864 | 4/1996 |
| JP | 9-018039 | 1/1997 |
| JP | 9-116163 | 5/1997 |
| JP | 9-508965 | 9/1997 |
| JP | 10-125924 | 5/1998 |
| JP | 11-251601 | 9/1999 |
| JP | 2984370 | 11/1999 |
| JP | 2000-174277 | 6/2000 |
| JP | 2000-516395 | 12/2000 |
| JP | 2003-327588 | 11/2003 |
| WO | 00/11725 | 3/2000 |

OTHER PUBLICATIONS

Decision of Refusal issued Mar. 25, 2009, in Japanese Application No. 2003-084816, filed Mar. 26, 2003 (with English translation).
Report on Reconsideration issued Jul. 2, 2009, in Japanese Application No. 2003-084816, filed Mar. 26, 2003 (with English translation).
Office Action issued Jun. 9, 2008, in Japanese Application No. 2003-084816, filed Mar. 26, 2003 (with English translation).
Ito, S., et al., "A New Synthesis of Benzoporphyrins using 4,7-dihydro-4,7-ethano-2H-isoindole as an Isoindole Equivalent", Heterocycles, vol. 52, No. 1, pp. 399-411 (2000).
Bao, Z., et al., "Organic Field-Effect Transistors with High Mobility Based on Copper Phthalacyanine", Appl. Phys. Lett., vol. 69, No. 20, pp. 3066-3068 (Nov. 11, 1996).
Brown, A.R., et al., "Logic Gates made from Polymer Transistors and their use in Ring Oscillators", Science, vol. 270, pp. 972-974 (Nov. 10, 1995).
Matters, M., et al "Organic Field-Effect Transistors and All-Polymer Integrated Circuits", Optical Materials, vol. 12, pp. 189-197, (1999).
Brown, A.R., et al., "Precursor Route Pentacene Metal-Insulator-Semiconductor Field-Effect Transistors", J. Appl. Phys., vol. 79, No. 4, pp. 2136-2138 (Feb. 15, 1996).
Yoshida, Y., et al., "Novel Techniques for Molecular Orientation Controlled Organic Devices", Proceedings of Second International Conference on Molecular Electronics and Bioelectronics (M&BE2), pp. 35-36 (Mar. 5-7, 2003).
Dahal, et al., "Solid State Supramolecular Chemistry of Prophyrins. Hydrogen-Bonded Networks and Porous Crystals of Meso-tetra[4-(3,5-diaminotriazino)phyenyl]porphyrin", Journal of Physical Organic Chemistry, vol. 13, pp. 382-387 (2000).
Checcoli, et al., Tetra-phenyl Porphyrin Based Thin Film Transistors, Proceedings Symp. E-MRS Spring Meeting 2002, Jun. 18-21, 2002, Strasbourg, France; later published in Synthetic Metals, vol. 138, Issues 1-2, pp. 261-266, Jun. 2, 2003.
Ito, S., et al., "As New Synthesis of Benzoporphyrins using 4,7-dihydro-4,7-ethano-2H-Isoindole as a Synthon of Isoindole", Chem. Commun., pp. 1661-1662 (1998).
Akiyama, T., et al., "Synthesis of Pal.-System Expanded Compounds using Diels-Alder Reactions" Chemical Society of Japan, No. 2F9-14, p. 990.
Herwig, P.T., et al., "A Soluble Pentacene Precursor: Synthesis Solid-State Conversion into Pentacene and Application in a Field-Effect Transistor", Advanced Material, vol. 11, No. 6, pp. 480-483 (1999).
Ono, N., "Synthesis and properties of new conjugated systems from II-extended pyrroles", Technical Report of Institute of Electronics, Information and Communication Engineers, OME, Organic Electronics, vol. 101, No. 103, pp. 1-6 (Mar. 25, 2001).
Japanese Office Action issued Mar. 13, 2012 in patent application No. 2009-124554 with English translation.
Satoshi Ito, et al., "Synthesis of a gable bis-porphyrin linked with a bicyclo[2.2.2]octadiene ring and its conversion into a conjugated planar bis-porphyrin", Chemical Communications, The Royal Society of Chemistry, Dec. 4, 2001, pp. 2696-2697.
Notice of Reason(s) for Refusal issued Dec. 5, 2011, in Japanese Patent Application No. 2008-205635 filed Aug. 8, 2008 (with English translation).
Decision of Refusal issued Oct. 9, 2008, in Japanese Patent Application No. 2002-104639 filed Apr. 8, 2002 (with English translation).
Reconsideration Report issued Apr. 2, 2009, in Japanese Patent Application No. 2002-104639 filed Apr. 8, 2002 (with English translation).
Notice of Reason(s) for Refusal issued Nov. 25, 2011, in Japanese Patent Application No. 2008-323252 filed Dec. 19, 2008 (with English translation).
H. Fuchigami, et al., Appl. Phys. Lett., vol. 63, No. 10, pp. 1372-1374 (Sep. 6, 1993).
K. Takahashi, et al., Solar Energy Materials and Solar Cells, vol. 45, pp. 127-139 (1997).

\* cited by examiner

..●.. Without a protective layer
—■— With a protective layer

METHOD FOR PRODUCING ORGANIC ELECTRONIC DEVICE INCLUDING CONVERTING A PRECURSOR FOR A SEMICONDUCTOR LAYER

The entire disclosures of Japanese Patent Application No. 2002-089425 filed on Mar. 27, 2002, Japanese Patent Application No. 2002-104639 filed on Apr. 8, 2002 and Japanese Patent Application No. 2003-049561 filed on Feb. 26, 2003 including specifications, claims, drawings and summaries are incorporated herein by reference in their entireties.

BACKGROUND OF THE INVENTION

1. Field of the Invention

The present invention relates to an organic semiconductor material and an organic electronic device such as a field effect transistor. Particularly, it relates to an organic semiconductor material comprising a generalized porphyrin compound having a specific structure, and an organic electronic device employing such a material.

2. Discussion of the Background

Heretofore, as a field effect transistor (hereinafter sometimes referred to as FET) device, one employing, as a semiconductor layer, an inorganic semiconductor material such as a silicon (Si) or gallium arsenide single crystal, has been widely used. However, in the case of an inorganic material, it will be treated at a high temperature of at least 300° C. at the time of its production, whereby it is difficult to employ a plastic (or resin) for the substrate, and a large energy is required for its production. It requires a production process under vacuum, such as vapor deposition, sputtering or CVD, whereby it is difficult to produce a device having a large surface area. Further, it requires an expensive installation in its production line, thus leading to a problem of a high cost, etc.

Under the circumstances, an organic electronic device has been proposed wherein an organic semiconductor material is used for a semiconductor layer of an electronic device such as a field effect transistor, a light emitting diode or a nonlinear optical device. According to such a proposal, such a semiconductor layer can be prepared by a relatively low temperature process, whereby a plastic film can be used as the substrate, and there is a merit such that a device which is light in weight, excellent in flexibility and scarcely breakable, can be prepared. Further, it can be formed by a coating method or a printing method, whereby there is a merit such that a device having a large area can be produced at low cost without necessity of an expensive installation. Further, the organic material is rich in variation, and it is possible to basically change the properties of the material by changing its molecular structure, whereby there is a possibility that it is possible to obtain a device having a function which an inorganic material can not provide.

Organic semiconductor materials may be classified broadly into two types i.e. high molecular compound material (a polymer material) and low molecular compound material. With respect to each of them, there is a report i.e. on a device employing a conductive high molecular compound or a conjugated high molecular compound (JP-A-61-202467), or on a device employing a low molecular compound (JP2984370).

As such a high molecular compound material, a conductive polymer or a conjugated polymer is, for example, typical, and it has been attempted to use a conjugated polymer compound as it is, as a semiconductor, or to carry out switching by applying an electric field to introduce or withdraw ions (dopants) to or from a conjugated polymer compound. However, there have been problems inherent to a polymer, such that the solubility in a solvent is low, whereby a uniform coating fluid can hardly be obtained, the film is poor in uniformity or stability, defects attributable to incomplete structural portions are likely to result during the film formation, the purification is difficult, and the oxidation potential tends to be low, whereby the material is susceptible to oxidation. Thus, a material having high performance and high stability has not yet been found.

Whereas, in the case of the low molecular compound, the structure of the compound obtainable as a result of the synthesis is substantially predetermined, and various purification methods such as sublimation purification, recrystallization, column chromatography, etc. can be used. Thus, it is superior in that the purity is high, and a material having high performance and high stability can readily be obtainable.

As an example of such a low molecular compound material, an aromatic condensed hydrocarbon compound such as pentacene or an oligothiophene having 4 or more thiophene rings chained, which as formed into a film by vapor deposition, shows a mobility as high as amorphous silicon (a-Si), has been reported. However, such a low molecular compound tends to be oxidized although not so much as the high molecular weight compound, and there is a problem from the viewpoint of the stability. Namely, oxygen in the air is likely to be doped to the organic semiconductor film, whereby it is likely that the carrier density increases, and the leakage current increases or the mobility changes, whereby constant characteristics can hardly be obtainable.

Further, the low molecular compound can hardly be one whereby the characteristics of an organic compound are sufficiently utilized, since a coating process is hardly applicable thereto, and it is required to employ a film-forming method by vapor deposition which makes the production cost high. Further, if the low molecular weight compound is formed into a film by coating of its solution, a uniform film can hardly be obtainable, since it will have a granular structure by crystallization, and thus, there will be many cases wherein there is a problem in the film forming properties.

For example, applications of phthalocyanines to field effect transistors have been reported (JP-A-11-251601, JP-A-2000-174277, Appl. Phys. Lett., vol. 69 (1996), p. 3,086). However, phthalocyanines are usually insoluble in solvents, to prepare such devices, and it is necessary to carry out film formation by a vacuum vapor deposition method.

Under the circumstances, methods have been reported in recent years wherein a precursor for a low molecular compound having a high solubility in a solvent, is dissolved in a solvent or the like, then formed into a film by a coating process and then converted to a semiconductor to obtain an organic semiconductor film, so that a field effective transistor is thereby prepared. For example, there are cases wherein pentacene or analogous aromatic hydrocarbons are employed (Science, vol. 270 (1995) p. 972, Optical Materials vol. 12 (1999), p. 139, J. Appln. Phys. Vol. 0.79 (1996) p. 2,136).

Here, the operation characteristics of a field effect transistor are determined mainly by the carrier mobility μ or electroconductivity of the semiconductor layer, the capacitance $C_i$ of the insulating layer, and the construction of the device (such as the source drain electrode distance L and width W, the thickness d of the insulating layer, etc.). Among them, it is important that the carrier mobility μ (hereinafter sometimes referred to simply as the mobility) of the semiconductor material to be used for the semiconductor layer, is high. With respect to pentacene, a case where the mobility is 0.2 cm²/Vs depending upon the condition of the film, has been reported. However, the mobility demonstrated by an actual application to a device has been at a level of $10^{-2}$ cm$^2$/Vs, and the mobility in the practical use is not yet high. Further, from the pentacene precursor in this case, a tetrachlorobenzene molecule will be detached, but tetrachlorobenzene is not only hardly removable from the reaction system as the boiling point is high, but also problematic in view of its toxicity.

Meanwhile, as a material for an optical device to obtain a photoelectric current or photoelectromotive force, a porphyrin compound has been studied, and an application of benzoporphyrin to a solar cell is disclosed in JP-A-9-18039. However, its carrier mobility is low, and when the mobility is calculated from the carrier density and the resistivity disclosed in Examples, it is still at a level of $1.3 \times 10^{-6}$ cm$^2$/Vs even at the maximum. Since the mobility is so low, the study on the application of the porphyrin compound has been limited to an optical device, and no application to an organic electronic device has been observed wherein all mobility or electromobility is positively utilized.

As described above, an organic semiconductor material has various characteristics which are not observed with an inorganic semiconductor material. However, organic semiconductor materials having relatively high performance, such as phthalocyanines, pentacenes or oligothiophenes, are all restricted in that the process for their production has been limited to a vapor deposition process which is highly costly. Therefore, it is desired to obtain an organic electronic device which can be produced by a simpler process and which, at the same time, has practical characteristics.

Accordingly, an organic semiconductor material which has high carrier mobility and stability and which can be formed into a film by a simple production process such as a coating process, and an organic electronic device employing such an organic semiconductor material, have been desired.

SUMMARY OF THE INVENTION

As a result of various studies made under the above circumstances, it has been found that an organic electronic device employing, as a semiconductor material, a compound having a certain specific porphyrin skeleton, is useful, and the present invention has been accomplished on the basis of this discovery. With respect to porphyrin, an application to a solar cell has been known. However, in that application, the mobility has been still inadequate, probably because purification of the porphyrin itself has been inadequate. Thus, heretofore, no attention has been drawn to a porphyrin compound as a material for an organic electronic device, since its synthesis or purification has been difficult.

However, as a result of the study on the application of a porphyrin compound by the present inventors, it has been surprisingly found that a compound having a certain specific generalized porphyrin skeleton can be formed into a film even by a solution process and shows a high mobility, and it thus presents an advantageous performance as compared with other organic semiconductor materials.

Namely, in a first aspect, the present invention provides an organic semiconductor material comprising a compound which has a generalized porphyrin skeleton and which has a molecular structure such that the distance from the generalized porphyrin ring plane to the center of each atom forming the generalized porphyrin skeleton, is not more than 1 Å.

In a second aspect, the present invention provides an organic semiconductor material comprising a compound which has a generalized porphyrin skeleton and which has a mobility of at least $1 \times 10^{-5}$ cm$^2$/Vs.

In a third aspect, the present invention provides an organic electronic device comprising a semiconductor layer and at least two electrodes, wherein the semiconductor layer contains the above organic semiconductor material.

DETAILED DESCRIPTION OF PREFERRED EMBODIMENTS OF THE INVENTION

Figure 1A:
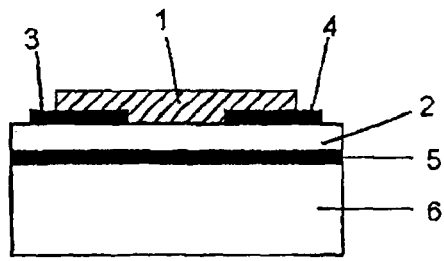
FIG. 1A to 1D are schematic views showing field effect transistors (FET) of the present invention.
Figure 1B:
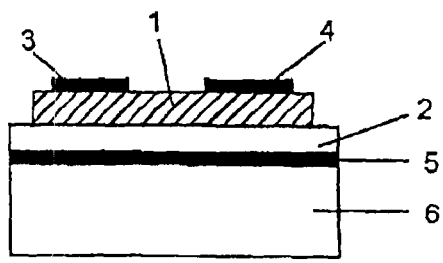
Figure 1C:
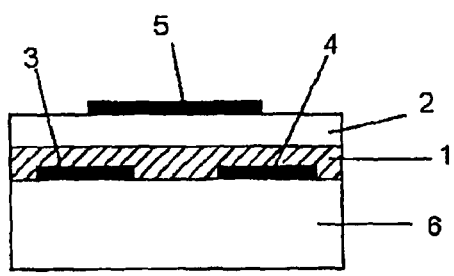
Figure 1D:
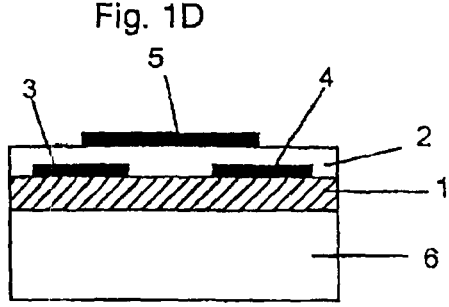

Now, preferred embodiments of the present invention will be described in detail.

Firstly, the organic semiconductor material of the present invention will be described. In the present invention, a compound having a specific generalized porphyrin skeleton, is employed.

Compound Having a Generalized Porphyrin Skeleton

In the present invention, the compound having a generalized porphyrin skeleton is a general term for a compound having a porphyrin skeleton and a compound having an expanded porphyrin skeleton, which is an analogue having the number of pyrrole rings forming a porphyrin skeleton increased or having a pyrrole ring replaced by e.g. a thiophene ring or a furan ring, and it is a concept including, for example, porphyrin type, thiaporphyrin type, dithiaporphyrin type, oxaporphyrin type, dioxaporphyrin type and thiaoxaporphyrin type compounds.

Specifically, in the present invention, the compound having a generalized porphyrin skeleton, is a compound containing a structure represented by the following formula (A).

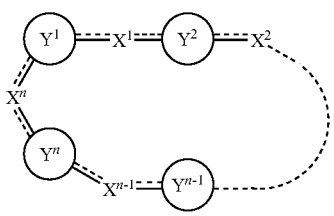

(A)

In the above formula, each of $Y^1$ to $Y^n$ which are independent of one another, is a π-conjugated single ring of hydrocarbon ring or heterocyclic ring, and each of $Y^1$ to $Y^n$ may be substituted. Each of $X^1$ to $X^n$ which are independent of one another, is a direct bond or a connecting group consisting of a linear hydrocarbon group, and each of $X^1$ to $X^n$ may be substituted. Here, the symbol ----- represents a single bond or a double bond. n is an integer of from 4 to 20. Further, in the structure represented by the above formula (A) as a whole, π-electron systems are conjugated in a ring form. Namely, the structure represented by the above formula is a structure in which π-conjugated rings represented by $Y^1$ to $Y^1$ are π-conjugated as a whole via $X^1$ to $X^n$. Accordingly, each of $Y^1$ to $Y^n$ is a planar unit, and the structure represented by the above formula (A) as a whole takes a structure having a very high planar nature.

For an organic semiconductor material to have high carrier mobility, it is desired that adjacent molecules well overlap each other in a solid state. Namely, for a carrier i.e. an electron or a hole to be transmitted between molecules, interaction between π-electron orbitals is important. It is well known that in an organic semiconductor, π-electrons play an important role for charge transport. However, substantially no case is known wherein π-electrons are conjugated to a macroscopic scale to show a semiconductor characteristic.

Particularly, in a molecular crystal, conjugation of π-electrons is limited within the molecule, and charge transport is done by the movement of an electric charge between molecules. In such a case, the greater the overlapping of π-orbitals conjugated within the molecules, the higher the efficiency of the charge transport. Therefore, the mobility of the molecular crystal will also have a directional dependency. Further, this is reflected also to the fact that usually, a highly crystalline material shows a higher mobility than an amorphous material.

In order to increase the overlapping of π-orbitals among molecules, it is desired that the planar nature of π-conjugated systems in the molecules, is high. As an index for the planar nature, the deviation of atoms forming the generalized porphyrin skeleton, from the generalized porphyrin ring plane, may be employed.

Accordingly, the present invention is characterized in that the distance from the generalized porphyrin ring plane to the center of each atom forming the generalized porphyrin skeleton, is not more than 1 Å. If this distance is within 1 Å, the conditions to increase the mobility and to provide a high planar nature, can be satisfied.

Here, "a generalized porphyrin ring" means a structure represented by the formula (A) comprising π-conjugated rings represented by $Y^1$ to $Y^n$ and $X^1$ to $X^n$. "The generalized porphyrin ring plane" means a plane such that the sum of squares of the distances from the centers of all atoms forming the generalized porphyrin ring, becomes minimum. Further, "the generalized porphyrin skeleton" includes, in addition to atoms forming the generalized porphyrin ring, an atom or atomic group which is bonded to the generalized porphyrin ring and which is restrained from free rotation by a thermal energy at a level of room temperature (i.e. 25° C.).

Here, "an atom or atomic group which is bonded to the generalized porphyrin ring and which is restrained from free rotation by a thermal energy at a level of room temperature" means a case where the energy barrier against internal rotation of the bond between an atom of the generalized porphyrin ring and an atom directly bonded thereto, is larger than the thermal energy at room temperature (usually 25° C.). For example, it is a case where the energy barrier against internal rotation is at least 10 kcal/mol.

Usually, the energy required for rotation of a bond can be obtained by actual measurement, but can also be obtained by calculation by e.g. a molecular orbital method. A non-empirical molecular orbital method such as 6-311G (dp), or a semi-empirical molecular orbital method such as MOPAC, may be employed. Each has its own merit, i.e. by the non-empirical molecular orbital method, the precision is good, and by the semi-empirical molecular orbital method, the calculation is relatively simple.

In a case where two or more generalized porphyrin rings which can be rotated freely each other are contained in one molecule, it is only required that the planar nature of each generalized porphyrin ring is good, and it is not required to take such a structure that the plurality of porphyrin skeletons contained in one molecule are in the same plane.

Now, the compound having a generalized porphyrin skeleton of the present invention will be described in further detail.

In the present invention, the compound having a generalized porphyrin skeleton means a compound containing a structure represented by the following formula (A):

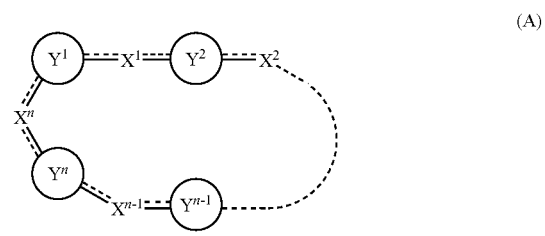

(A)

In the above formula, each of $Y^1$ to $Y^n$ which are independent of one another, is a π-conjugated single ring of hydrocarbon ring or heterocyclic ring, and each of $Y^1$ to $Y^n$ may be substituted. Each of $X^1$ to $X^n$ which are independent of one another, is a direct bond or a connecting group consisting of a linear hydrocarbon group, and each of $X^1$ to $X^n$ may be substituted. Here, the symbol ----- represents a single bond or a double bond. n is an integer of from 4 to 20. Further, in the structure represented by the above formula (A) as a whole, π-electron systems are conjugated in a ring form.

Preferably, n is an integer of from 4 to 10, more preferably, n is an integer of from 4 to 6, and most preferably, n is 4. n represents the number of π-conjugated rings Y in the above structure, but if n is too large, the planar nature tends to deteriorate, the electrical properties tend to deteriorate, and the synthesis tends to be difficult.

In the above formula (A), each of $Y^1$ to $Y^n$ which are independent of one another, is a π-conjugated single ring of hydrocarbon ring or heterocyclic ring group, and each of $Y^1$ to $Y^n$ may have a substituent, but is preferably a 5- to 8-membered single ring. It is more preferably a 5- or 6-membered ring. Further preferably, it is a 5-membered ring.

Preferred specific examples for $Y^1$ to $Y^n$ will be shown below, but $Y^1$ to $Y^n$ are not limited thereto. A 5-membered ring may, for example, be a pyrrole ring, a thiophene ring, a furan ring, a dithiazole ring, a dithiazole ring, an oxazole ring, an oxadiazole ring, a selenophene ring or a cyclopentadiene ring. A 6-membered ring may, for example, be a benzene ring, a pyridine ring, a pyrimidine ring, a naphthalene ring, an anthracene ring or a pyrene ring.

Each of $Y^1$ to $Y^n$ may have a substituent. For example, each of $Y^1$ to $Y^n$ may be condensed with another hydrocarbon ring or heterocyclic ring to form a condensed ring. Such another ring is preferably an aromatic ring, whereby the planar nature will be increased. Further, such another ring is preferably a 5- to 8-membered ring, more preferably a 5- or 6-membered ring.

Hereinafter, the single rings of $Y^1$ to $Y^n$ or the condensed rings made of $Y^1$ to $Y^n$ and another ring, will be generally referred to as rings containing $Y^1$ to $Y^n$. Each of rings containing $Y^1$ to $Y^n$ is preferably a single ring or a 2- to 8-condensed ring, more preferably a single ring or a 2- to 6-condensed ring, most preferably a single ring or a 2- to 4-condensed ring. It is particularly preferred that all rings containing $Y^1$ to $Y^n$ are aromatic rings, whereby the planar nature will be increased.

A preferred example of such another ring is a π-conjugated ring such as benzene, naphthalene, anthracene, pyridine or quinoline. The condensed ring made of $Y^1$ to $Y^n$ and another ring may specifically be, for example, a benzopyrrole ring, a benzothiophene ring or a benzofuran ring.

On the other hand, an undesirable example of such another ring is typically a bicyclo ring.

The rings containing $Y^1$ to $Y^n$ may have substituents. The following groups may be mentioned as specific examples of the substituents which the rings containing $Y^1$ to $Y^n$ may have:

A $C_{1-18}$ linear or branched alkyl group which may be substituted, such as a methyl group, an ethyl group, a propyl group, an isopropyl group, a n-butyl group, a sec-butyl group, a tert-butyl group or a n-heptyl group; a $C_{3-18}$ cyclic alkyl group which may be substituted, such as a cyclopropyl group, a cyclopentyl group, a cyclohexyl group or an adamantyl group; a $C_{2-18}$ linear or branched alkenyl group which may be substituted, such as a vinyl group, a propenyl group or a hexenyl group; a $C_{3-18}$ cyclic alkenyl group which may be substituted, such as a cyclopentenyl group or a cyclohexenyl group; a $C_{2-18}$ linear or branched alkynyl group which may be substituted, such as a propynyl group or a hexynyl group; a heterocyclic group which may be substituted, such as a 2-thienyl group, a 2-pyridyl group, a 4-piperidyl group or a morpholino group; a $C_{6-18}$ aryl group which may be substituted, such as a phenyl group, a tolyl group, a xylyl group or a mesityl group; a $C_{7-20}$ aralkyl group which may be substituted, such as a benzyl group or a phenethyl group; a $C_{1-18}$ linear or branched alkoxy group which may be substituted, such as a methoxy group, an ethoxy group, a n-propoxy group, an isopropoxy group, a n-butoxy group, a sec-butoxy group or a tert-butoxy group; a $C_{3-18}$ linear or branched alkenyloxy group which may be substituted, such as a propenyloxy group, a butenyloxy group or a pentenyloxy group; and a $C_{1-18}$ linear or branched alkylthio group (mercapto group) which may be substituted, such as a methylthio group, an ethylthio group, a n-propylthio group, a n-butylthio group, a sec-butylthio group or a tert-butylthio group.

Other specific examples may, for example, be a halogen atom such as a fluorine atom, a chlorine atom or a bromine atom; a nitro group; a nitroso group; a cyano group; an isocyano group; a cyanate group; an isocyanate group; a thiocyanate group; an isothiocyanate group; a mercapto group; a hydroxy group; a hydroxyamino group; a formyl group; a sulfonate group; a carboxyl group; an acyl group represented by —$COR^6$, an amino group represented by —$NR^7R^8$, an acylamino group represented by —$NHCOR^9$, a carbamate group represented by —$NHCOOR^{10}$, a carboxylate group represented by —$COOR^{11}$, an acyloxy group represented by —$OCOR^{12}$, a carbamoyl group represented by —$CONR^{13}R^{14}$, a sulfonyl group represented by —$SO_2R^{15}$, a sulfamoyl group represented by —$SO_2NR^{16}R^{17}$, a sulfonate group represented by —$SO_3R^{18}$, a sulfoneamide group represented by —$NHSO_2R^9$, and a sulfinyl group represented by —$SOR^{20}$. Here, each of $R^6$, $R^9$, $R^{10}$, $R^{11}$, $R^{12}$, $R^{15}$, $R^{18}$, $R^{19}$ and $R^{20}$ is a hydrocarbon group which may be substituted, or a heterocyclic group which may be substituted, and each of $R^7$, $R^8$, $R^{13}$, $R^{14}$, $R^{16}$ and $R^{17}$ is a hydrogen atom, a hydrocarbon group which may be substituted or a heterocyclic group which may be substituted.

The hydrocarbon group represented by each of $R^6$ to $R^{20}$ is a linear or branched alkyl group, a cyclic alkyl group, a linear or branched alkenyl group, a cyclic alkenyl group, an aralkyl group or an aryl group. It is preferably a $C_{1-18}$ linear or branched alkyl group such as a methyl group, an ethyl group, a propyl group, an isopropyl group, a n-butyl group, a sec-butyl group, a tert-butyl group or a n-heptyl group, a $C_{3-18}$ cyclic alkyl group such as a cyclopropyl group, a cyclopentyl group, a cyclohexyl group or an adamantyl group, a $C_{2-18}$ linear or branched alkenyl group such as a vinyl group, a propenyl group or a hexenyl group, a $C_{3-18}$ cyclic alkenyl group such as a cyclopentenyl group or a cyclohexenyl group, a $C_{7-20}$ aralkyl group such as a benzyl group or a phenethyl group, or a $C_{6-18}$ aryl group such as a phenyl group, a tolyl group, a xylyl group or a mesityl group. The aryl group moiety of such a group may further be substituted by the same substituent as for the above-described rings containing $Y^1$ to $Y^n$.

The heterocyclic group represented by each of $R^6$ to $R^{20}$ may, for example, be a saturated heterocyclic group such as a 4-piperidyl group, a morpholino group, a 2-morpholinyl group or a piperazyl group, or an aromatic heterocyclic group such as a 2-furyl group, a 2-pyridyl group, a 2-thiazolyl group or a 2-quinolyl group. Such a group may contain a plurality of hetero atoms and may further have a substituent at any position. One having a preferred structure as the heterocyclic ring, is a 5- or 6-membered saturated heterocyclic ring or an aromatic heterocyclic ring which is a 5- or 6-membered single ring or a condensed ring composed of two such 5- or 6-membered rings.

The linear or branched alkyl group, the cyclic alkyl group, the linear or branched alkenyl group, the cyclic alkenyl group, the linear or branched alkynyl group, the linear or branched alkoxy group, or the linear or branched alkylthio group, which the above-mentioned rings containing $Y^1$ to $Y^n$ may have, and the alkyl chain moiety of the alkyl group represented by each of $R^6$ to $R^{20}$, may further have a substituent, and such a substituent may, for example, be as follows. A $C_{1-10}$ alkoxy group such as a methoxy group, an ethoxy group, a n-propoxy group, an isopropoxy group, a n-butoxy group, a sec-butoxy group or a tert-butoxy group; a $C_{2-12}$ alkoxyalkoxy group such as a methoxymethoxy group, an ethoxymethoxy group, a propoxymethoxy group, an ethoxyethoxy group, a propoxyethoxy group or a methoxybutoxy group; a $C_{3-15}$ alkoxyalkoxyalkoxy group such as a methoxymethoxymethoxy group, a methoxymethoxyethoxy group, a methoxyethoxymethoxy group, a methoxymethoxyethoxy group or an ethoxyethoxymethoxy group; a $C_{6-12}$ aryl group such as a phenyl group, a tolyl group or a xylyl group (which may be further substituted by an optional substituent);

a $C_{6-12}$ aryloxy group such as a phenoxy group, a tolyloxy group, a xylyloxy group or a naphthyloxy group; and a $C_{2-12}$ alkenyloxy group such as an allyloxy group or a vinyloxy group.

Further, other substituents may, for example, be a heterocyclic group such as a 2-thienyl group, a 2-pyridyl group, a 4-piperidyl group or a morpholino group; a cyano group; a nitro group; a hydroxyl group; an amino group; a $C_{1-10}$ alkylamino group such as an N,N-dimethylamino group or an N,N-diethylamino group; a $C_{1-6}$ alkylsulfonylamino group such as a methylsulfonylamino group, an ethylsulfonylamino group or a n-propylsulfonylamino group; a halogen atom such as a fluorine atom, a chlorine atom or a bromine atom; a $C_{2-7}$ alkoxycarbonyl group such as a carboxyl group, a methoxycarbonyl group, an ethoxycarbonyl group, a n-propoxycarbonyl group, an isopropoxycarbonyl group or a n-butoxycarbonyl group; a $C_{2-7}$ alkylcarbonyloxy group such as a methylcarbonyloxy group, an ethylcarbonyloxy group, a n-propylcarbonyloxy group, an isopropylcarbonyloxy group or a n-butylcarbonyloxy group; and a $C_{2-7}$ alkoxycarbonyloxy group such as a methoxycarbonyloxy group, an ethoxycarbonyloxy group, a n-propoxycarbonyloxy group, an isopropoxycarbonyloxy group or a n-butoxycarbonyloxy group.

Preferred among the substituents which the rings containing $Y^1$ to $Y^n$ may have, may, for example, be a hydroxyl group, a $C_{1-10}$ alkyl, alkoxy, mercapto or acyl group, which may be substituted, a carboxyl group or its ester with a $C_{1-10}$ alcohol, a formyl group, a carbamoyl group, a halogen atom such as fluorine, chlorine, bromine or iodine, an amino group which may be substituted by a $C_{1-10}$ alkyl group, or a nitro group. Such a preferred group may further have a substituent. For example, an alkyl moiety of such a substituent may further be substituted by a single atom such as a halogen atom.

Most preferably, each of rings containing $Y^1$ to $Y^n$ is unsubstituted or has a substituent composed of a single atom such as a halogen atom.

Each of $X^1$ to $X^n$ which are independent of one another, is a direct bond or a connecting group consisting of a linear hydrocarbon group, and each of $X^1$ to $X^n$ may be substituted. The linear hydrocarbon group is preferably one having from 1 to 10 carbon atoms, more preferably from L to 5 carbon atoms. More preferably, it is a $C_{1-3}$ unsaturated linear hydrocarbon group, particularly preferably, an alkenylene group, an alkynylene group, an alkanediylidene group or an alkenediylidene group.

Preferred specific examples for $X^1$ to $X^n$ include a methene group, a vinylene group (an ethenylene group), an ethynylene group and (=C=C=), but are not limited thereto. Further, each may have a substituent, although such a substituent is omitted in the above examples.

Specific examples of the substituents which $X^1$ to $X^n$ may have, may be roughly the same as the substituents which the rings containing $Y^1$ to $Y^n$ may have. However, bulky substituents which hinder free rotation, are undesirable. Preferred substituents may be a linear alkyl group which may be substituted, a linear alkoxy group, a linear mercapto group, an ester of a carboxyl group with a $C_{1-10}$ alcohol, or a halogen atom. The substituents which $X^1$ to $X^n$ may have, may be bonded to each other to form a ring.

Particularly preferred among them may be an unsubstituted linear alkyl group, a linear alkoxy group, a linear alkylthio group, an ester of a carboxyl group with a $C_{1-10}$ linear alcohol, or a halogen atom.

Most preferably, $X^1$ to $X^n$ are unsubstituted or have a substituent composed of a single atom such as a halogen atom.

On the other hand, a typical example of an undesirable substituent is a phenyl group.

Further, in the structure represented by the formula (A) as a whole, it is necessary that π-electron systems are conjugated in a ring form.

Further, the compound having a generalized porphyrin skeleton of the present invention, may have various metals, cations, anions, salts, etc., coordinated to some or all of $Y^1$ to $Y^n$ in the above structure. For example, a bivalent metal atom may be mentioned, and specific examples include Zn, Cu, Fe, Ni and Co. Further, an atomic group having a trivalent or higher valent metal and another atom bonded, such as Fe—$B^1$, Al—$B^2$, Ti=O or Si—$B^1B^4$, may, for example, be mentioned. Here, each of $B^1$, $B^2$, $B^3$ and $B^4$ is a monovalent group such as a halogen atom, an alkyl group or an alkoxy group.

Examples of such porphyrin type and expanded porphyrin type compounds are disclosed, for example, in THE PORPHYRIN HANDBOOK, VOL. 1-10, ACADEMIC PRESS (2000), edited by KARL M. KADISH KEVIN, M. SMITH ROGER GUILARD.

Further, it may be one wherein the same or different two generalized porphyrin rings are commonly conjugated to one atom, one wherein the same or different two generalized porphyrin rings are bonded via at least one atom or atomic group, or one wherein the same or different at least three generalized porphyrin rings are bonded in the form of a long chain.

As the compound having a generalized porphyrin skeleton of the present invention, most preferred is specifically one containing a structure represented by the following formula (1) or (2).

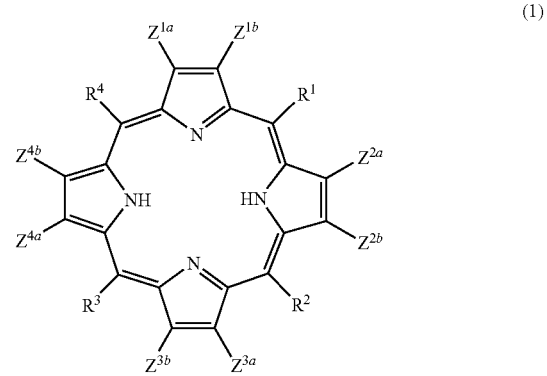

(1)

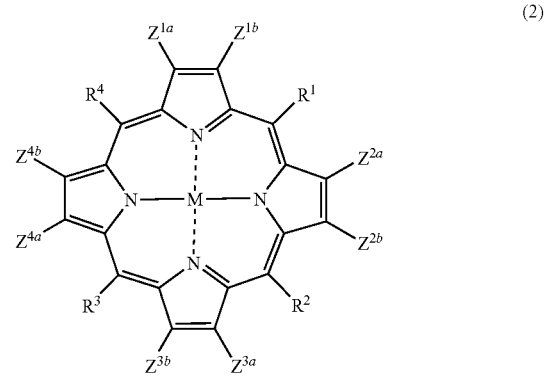

(2)

In the above formulae (1) and (2), each of $Z^{ia}$ and $Z^{ib}$ (i=1 to 4) represents a monovalent organic group, and $Z^{ia}$ and $Z^{ib}$ may be bonded to form a ring. The monovalent organic group may, for example, be a hydrogen atom, a hydroxyl group, a $C_{1-10}$ alkyl group which may be substituted, an alkoxy group, a mercapto group, an acyl group, a carboxyl group or its ester with a $C_{1-10}$ alcohol, a formyl group, a carbamoyl group, a halogen atom such as fluorine, chlorine, bromine or iodine, an amino group which may be substituted by a $C_{1-10}$ alkyl group, or a nitro group, and such a group may further have a substituent. Further, as an example of the organic group wherein $Z^{ia}$ and $Z^{ib}$ are bonded to form a ring, the ring formed by the structure $Z^{ia}$-CH=CH-$Z^{ib}$, may, for example, be an aromatic hydrocarbon such as a benzene ring, a naphthalene ring or an anthracene ring, a heterocyclic ring such as a pyridine ring, a quinoline ring, a furan ring or a thiophene ring, or a non-aromatic cyclic hydrocarbon such as a cyclohexene. Further, each of $R^1$ to $R^4$ is a hydrogen atom or a monovalent organic group.

Such an organic group may, for example, be an alkyl group which may be substituted, an aryl group, an alkoxy group, a mercapto group, an ester of a carboxyl group with a $C_{1-10}$ alcohol, or a halogen atom.

Further, M is a bivalent metal atom, such as Zn, Cu, Fe, Ni or Co, or an atomic group having a trivalent or higher valent metal and another atom bonded, such as Fe—$B^1$, Al—$B^2$, Ti=O or Si—$B^3B4$. Here, each of $B^1$, $B^2$, $B^3$ and $B^4$ is a monovalent group such as a halogen atom, an alkyl group or an alkoxy group.

Further, there may be one wherein two porphyrin rings are commonly coordinated to one atom, one wherein two porphyrin rings are bonded via at least one atom or atomic group, or one wherein at least three such porphyrin rings are bonded in the form of a long chain.

As mentioned above, in order to increase overlapping of the π-orbitals between molecules, the porphyrin compound of the present invention is preferably one wherein the planar nature of the π-conjugated systems in the molecule is high, and it is characterized in that it has a molecular structure wherein the distance from the porphyrin ring plane to the center of each atom forming the porphyrin skeleton, is not more than 1 Å. The atoms forming the porphyrin skeleton include, in addition to atoms forming the porphyrin ring, an atom or atomic group which is bonded to a substituent $Z^{ia}$, $Z^{ib}$ or $R^1$ to $R^4$ of (1) or (2), and free rotation of which by a thermal energy at a level of room temperature is restrained.

For example, carbon atoms forming four benzene rings or a tetraphenylporphyrin having the benzene rings bonded at four meso positions of a porphyrin ring, are restrained from free rotation due to steric hindrance between the benzene rings and the porphyrin ring, and thus, they are included in the porphyrin skeleton. It is not desirable that such groups are present at positions deviated from the plane of the porphyrin ring, since they tend to hinder overlapping of porphyrin rings by the steric hindrance. On the other hand, in a case where rotation of the bond is free as in the case of an alkyl group or an alkoxy group, especially a linear alkyl group or a linear alkoxy group, the structure can freely be adjusted so that the porphyrin rings can be overlapped, and such a group will not be a hindrance and therefore is not included in the porphyrin skeleton.

The porphyrin ring plane can be defined as such a plane that the sum of squares of the distances from the centers of all atoms forming the porphyrin ring, would be minimum. If the distance from this plane to the centers of atoms forming the porphyrin skeleton, is within 1 Å, it is possible to satisfy the conditions that the planar nature is high, and the mobility is high.

As typical examples of the generalized porphyrin compound not having a high planar nature, the following tetraphenylporphyrin, which is most well known as a porphyrin, and a porphyrin including bicyclo structure may be mentioned.

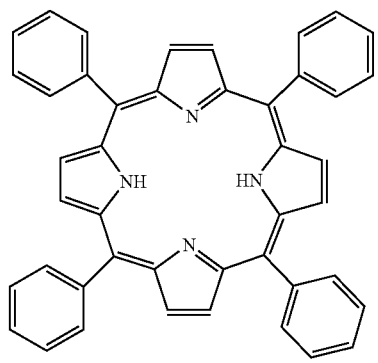

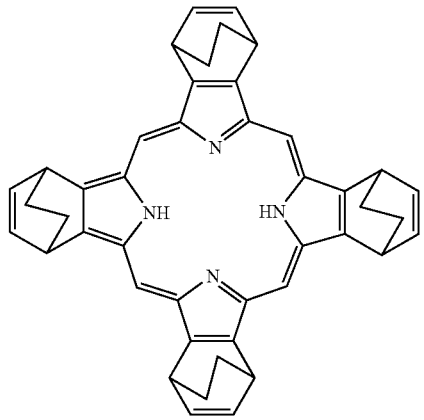

Accordingly, $Z^{ia}$ or $Z^{ib}$ in the above formula (1) or (2) is preferably a single atom such as a hydrogen atom or a halogen atom. Further, it may also be preferably a group forming a ring having a high planar nature and having no substituent, particularly one wherein at least one of $Z^{ia}$-CH=CH-$Z^{ib}$ (i=1 to 4) is a group forming an aromatic ring such as benzene, naphthalene or anthracene, or one wherein all of $Z^{ia}$-CH=CH-$Z^{ib}$ (i=1 to 4) are aromatic rings. Further, each of $R^1$ to $R^4$ is preferably a single atom such as a hydrogen atom or a halogen atom.

In the present invention, the organic semiconductor material is also characterized in that it comprises a compound which has a generalized porphyrin skeleton and which has a carrier mobility (mobility: μ) of at least $1 \times 10^{-5}$ cm$^2$/Vs.

The carrier mobility required for application to an electronic device is determined from the degree of the electric current to be controlled, the switching speed and the structure of the device. By using the generalized porphyrin compound of the present invention, it is possible to provide an organic device having a carrier mobility of at least $1\times10^{-5}$ cm$^2$/Vs, preferably at least $1\times10^{-3}$ cm$^2$/Vs. The mobility of a conventional organic semiconductor of molecular crystal is at a level of about 1 cm$^2$/Vs with a single crystal of an aromatic condensed hydrocarbon such as pentacene. A porphyrin molecule has π-orbitals which are substantially expanded, whereby there is a possibility that the interaction between molecules can be increased, and further, a center metal is present, whereby it can be expected to utilize the interaction via the metal, and thus it is considered possible to accomplish a mobility of from 10 cm$^2$/Vs to 100 cm$^2$/Vs.

The purity of the semiconductor material constituting the semiconductor layer may be mentioned as another condition for the high mobility. An impurity which traps the carrier causes a substantial deterioration of the mobility even in a trace amount. An impurity which is likely to form such a trap, is one having a level to receive the carrier in the energy gap of the semiconductor. When the carrier is a hole, it is one having the highest occupied molecular orbital (HOMO) level higher than the semiconductor, and when the carrier is an electron, it is one having the lowest unoccupied molecular orbital (LUMO) level lower than the semiconductor.

Even an impurity which presents no such an energy level, will cause a deterioration of the mobility, if the concentration becomes high to bring about a defect in the crystal structure of the semiconductor. Accordingly, the concentration of impurities is desired to be low, preferably at most 10%, more preferably at most 1%. The process of employing a precursor having a high solubility, which will be described hereinafter, has a merit in that it is thereby possible to form a semiconductor layer of high purity.

With a generalized porphyrin compound, a hole will usually be a carrier, but an electron may be made to be a carrier, as electron transport properties are provided by a substituent or by the center metal.

In a case where injection of electric charge from an electrode is required to take place smoothly as in the case of a field effect transistor, a preferred position is present for the energy level of the carrier. In the case of a hole, if HOMO is too low, the barrier against injection of the electric charge tends to be substantial, such being undesirable. On the other hand, if HOMO is too high, the material tends to be susceptible to oxidation by the air and tends to be unstable. Accordingly, the ionization potential in the solid state corresponding to the HOMO level is preferably at most 5.6 eV, more preferably at most 5.3 eV. Further, the ionization potential is preferably at least 4.5 eV, more preferably at least 4.8 eV.

The compound having a generalized porphyrin skeleton of the present invention is preferably in a solid state at room temperature for application to a device. Depending upon the substituent in the formula (1) or (2), a compound showing a liquid crystal property can be obtained, and it can be used as an organic semiconductor even in a liquid crystal state. Especially, the generalized porphyrin compound of the present invention has a structure having a good planar nature, whereby it is expected that a discotic liquid crystal may be obtained, and such a structure is suitable for transport of a carrier. It is not desirable that a substantial change in the properties will take place within the operational temperature range. Accordingly, a compound is preferred, of which the phase transfer temperature such as a melting point or a solidification point is not within a range of from 5° C. to 40° C. The compound which is in a solid state at room temperature is preferably such that the melting point or the glass transition point is at least 50° C., more preferably at least 100° C.

Further, the ON/OFF ratio of the organic semiconductor material comprising the generalized porphyrin compound of the present invention is desirably as high as possible, preferably at least 800, more preferably at least 1,000.

Now, examples of preferred generalized porphyrin compounds of the present invention will be given. Here, structures containing no metal are exemplified. However, metal salts corresponding to the following examples or the corresponding molecules having substituents may likewise be used as preferred examples. Further, molecular structures having good symmetry are mainly exemplified, but asymmetrical structures by a combination of partial structures, can also be used. The porphyrin compounds of the present invention are, of course, not limited to these exemplified compounds.

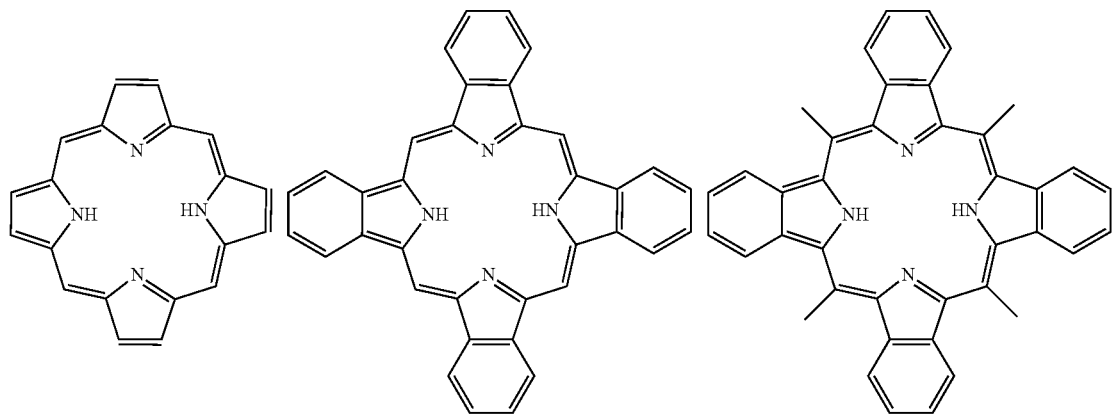

-continued
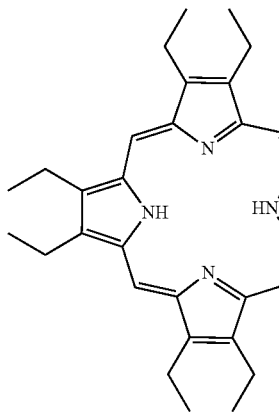
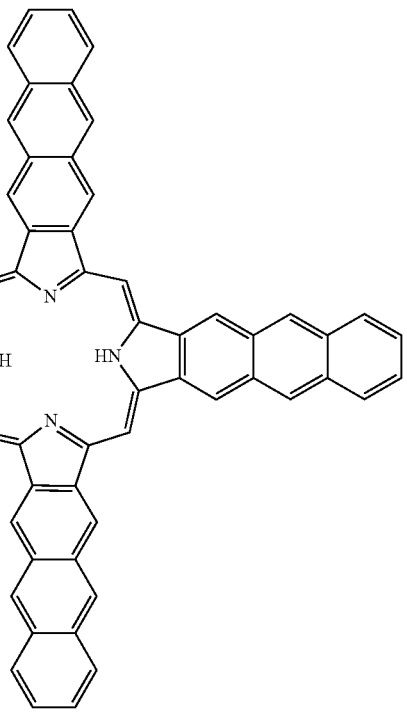
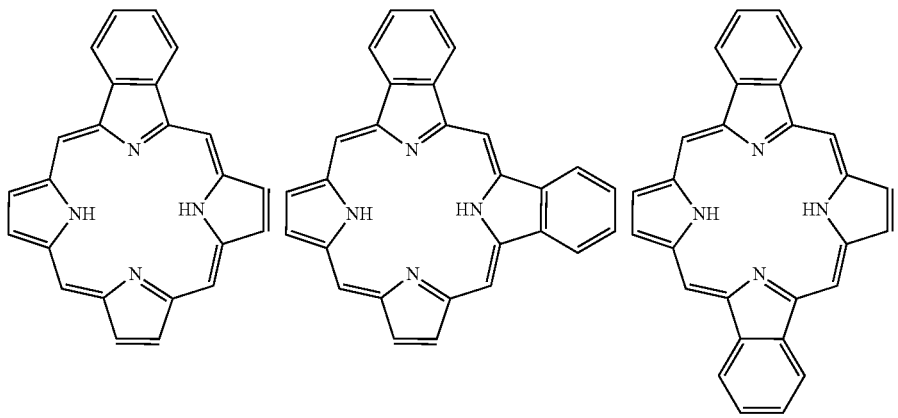
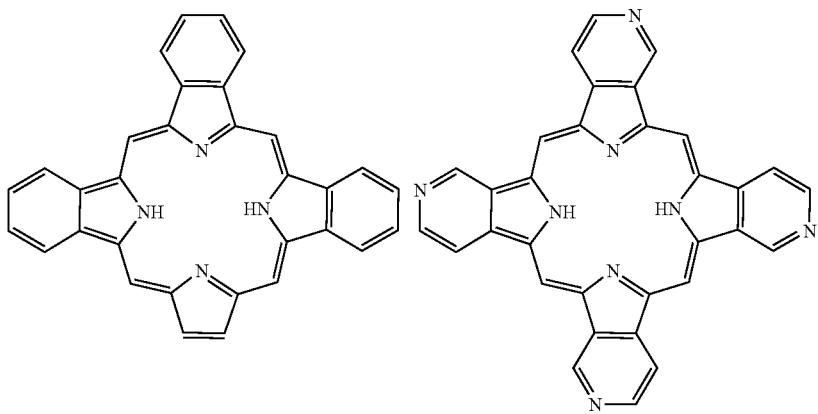

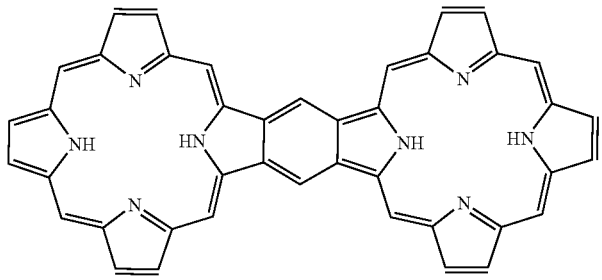
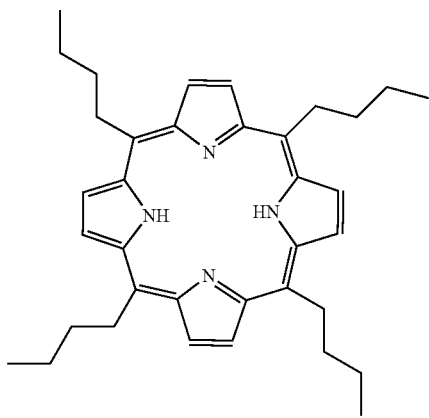
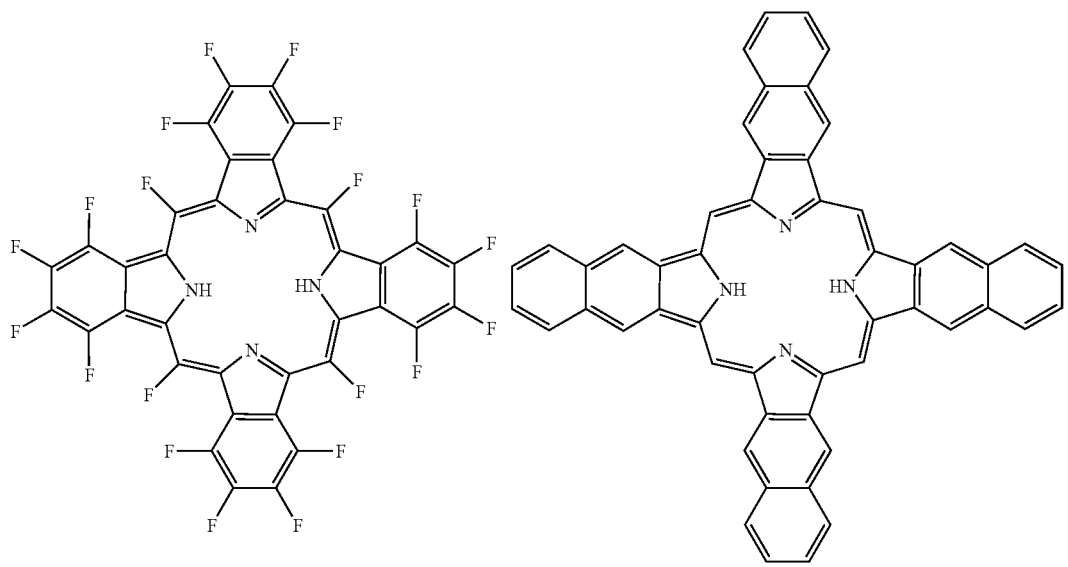
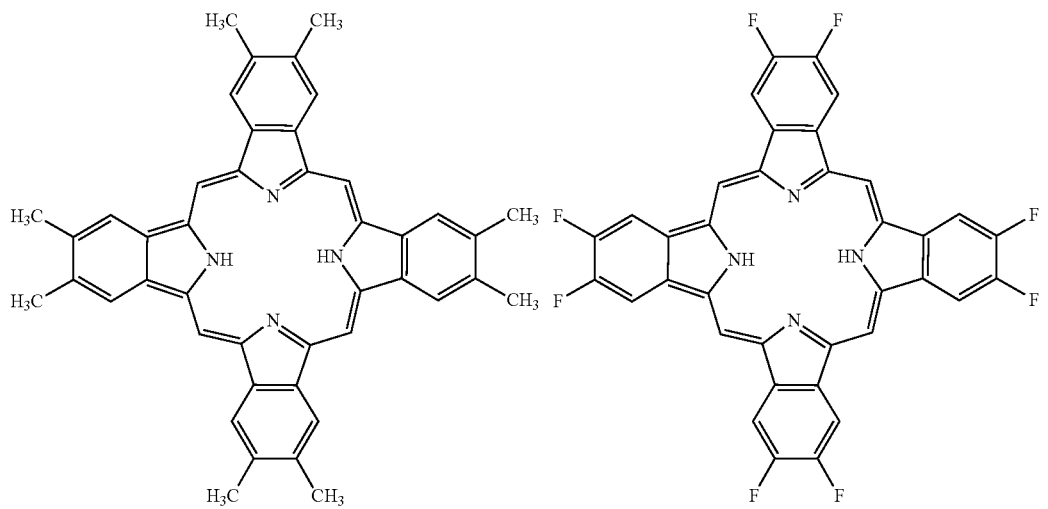

-continued
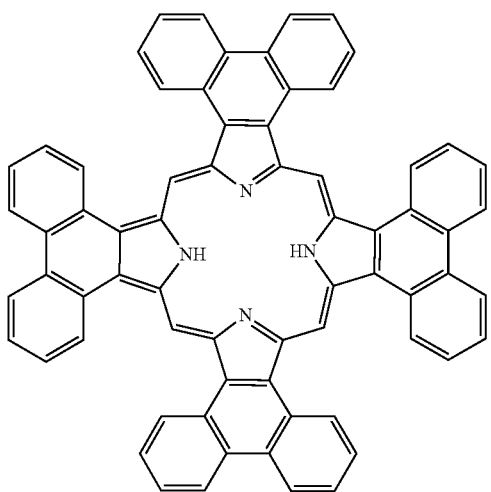
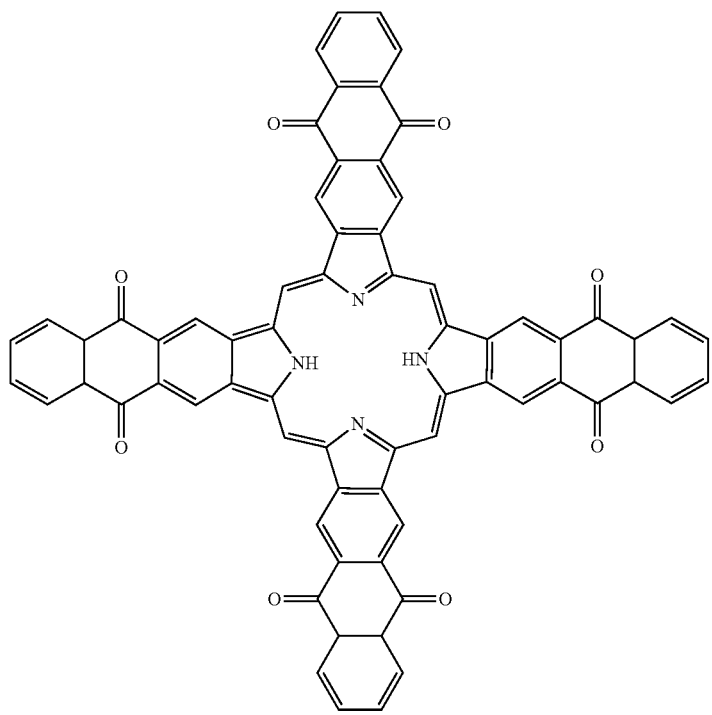
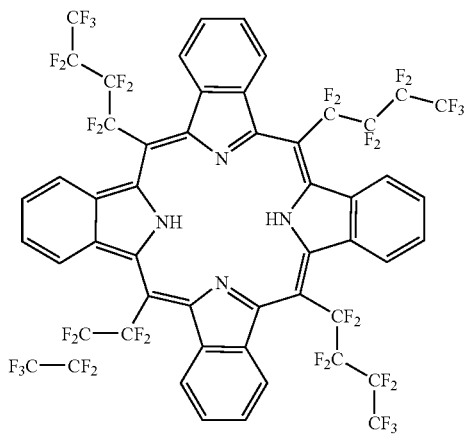
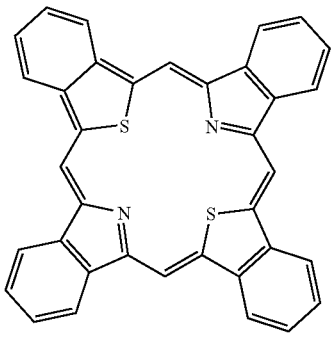
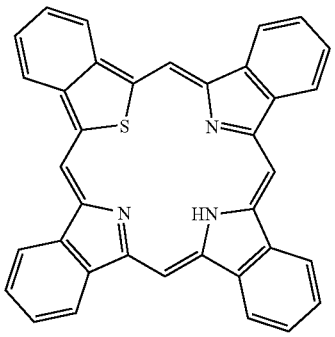

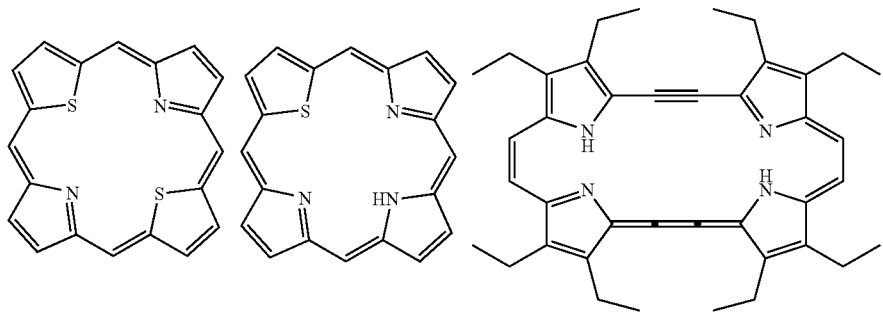
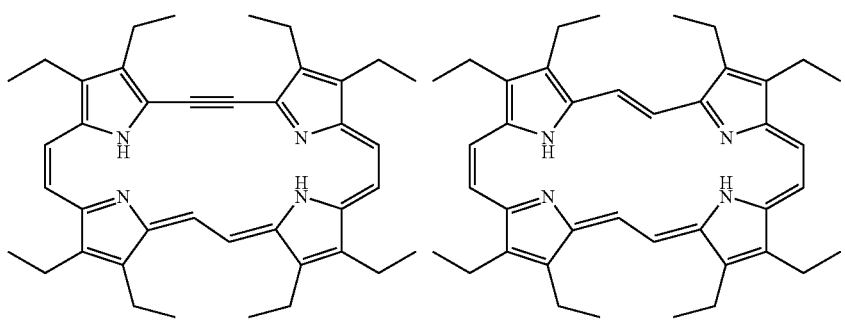
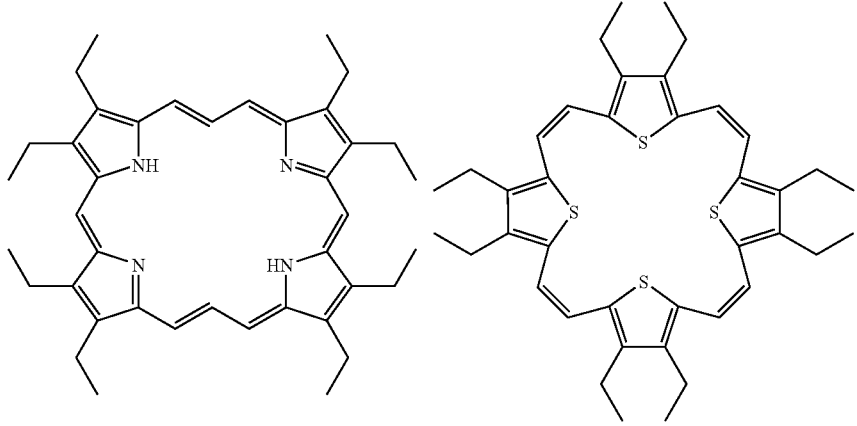
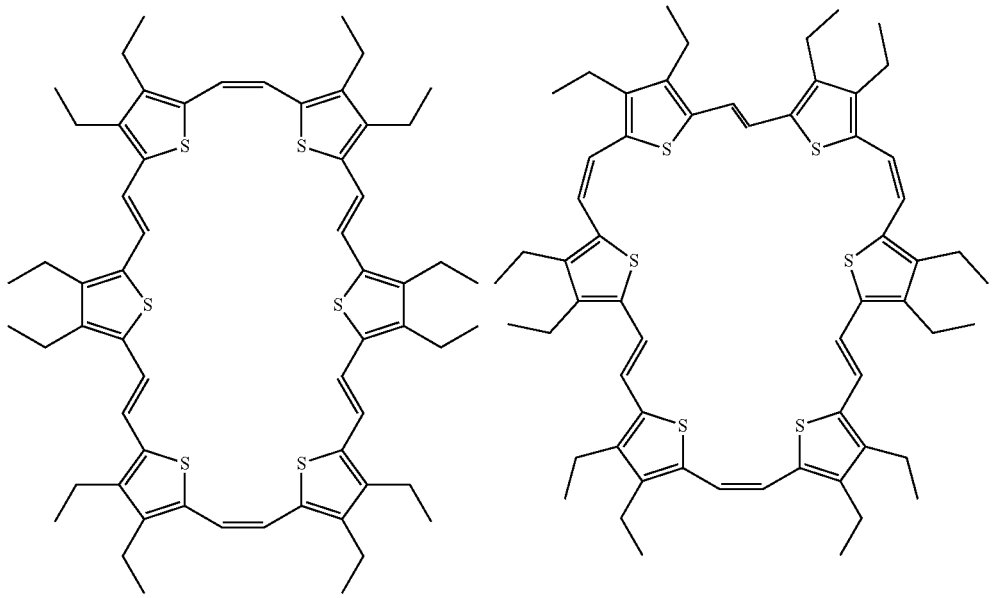

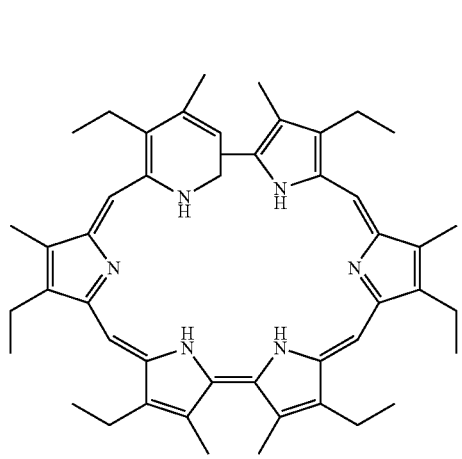
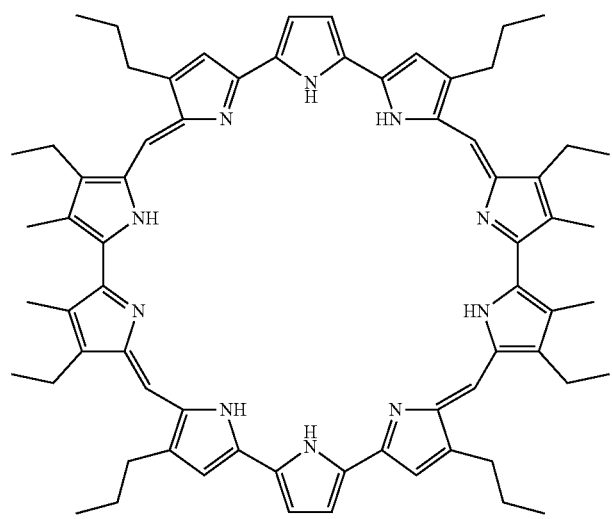
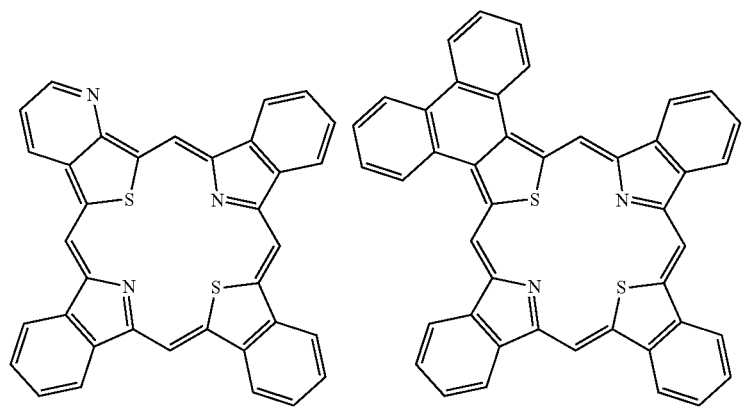
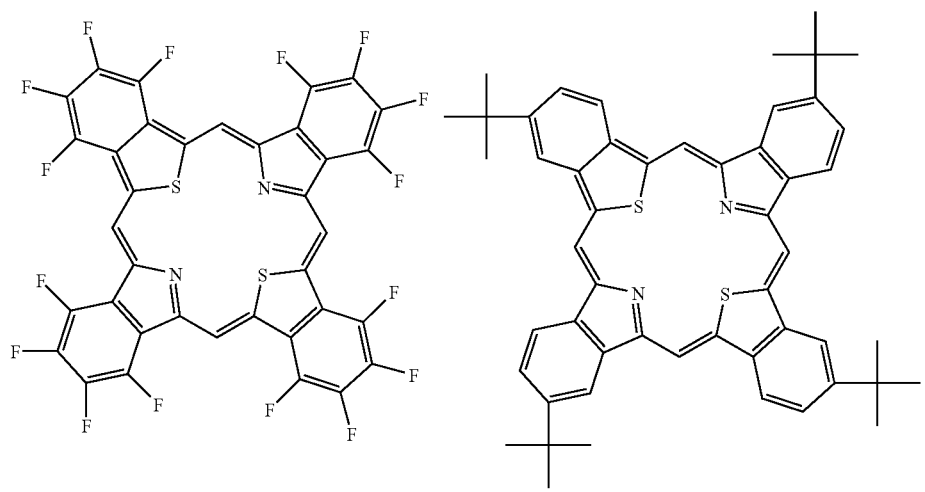

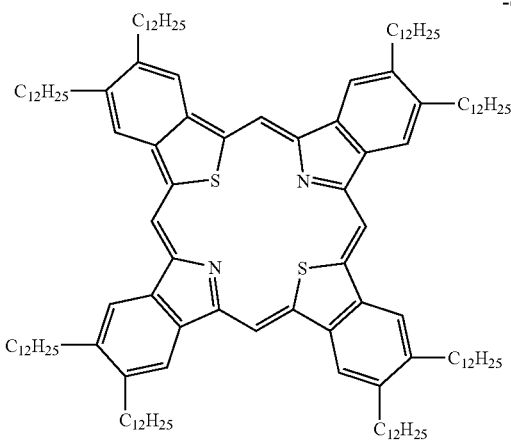
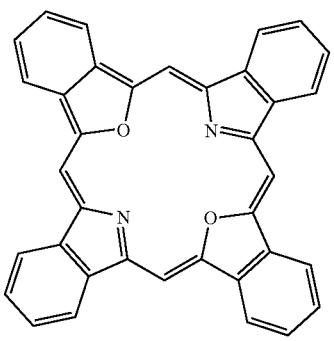
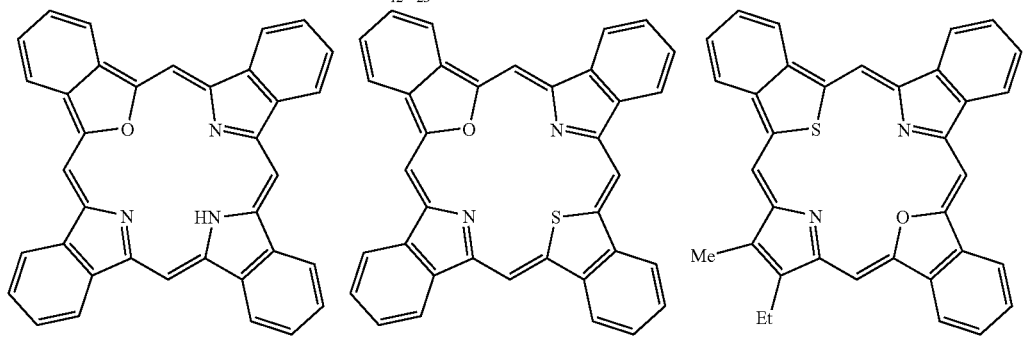

Synthesis of the Generalized Porphyrin Compound

The generalized porphyrin compound of the present invention can be synthesized by using the corresponding pyrrole compound, thiophene compound, furan compound or the like, as the starting material. For the synthesis of the generalized porphyrin compound, a method disclosed in THE PORPHYRIN HANDBOOK, VOL. 1, ACADEMIC PRESS (2000), edited by KARL M. KADIS H KEVIN M. SMITH ROGER GUILARD, may, for example, be used.

For example, condensation of pyrrole and an aldehyde, is frequently used particularly as a synthesis of a tetraphenylporphyrin.

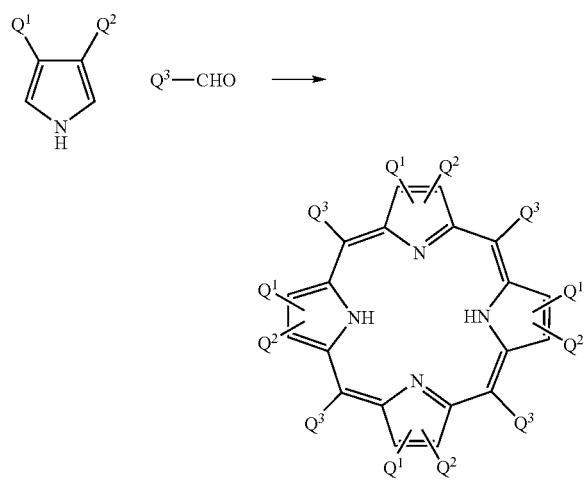

In the above formula, $Q^1$ and $Q^2$ correspond to $Z^{ia}$ and $Z^{ib}$ in the formula (1) or (2), and $Q^3$ corresponds to $R^1$ to $R^4$.

Further, it can be obtained also by a condensation reaction of a pyrrole having a carboxylate or a methyl group at the α-position.

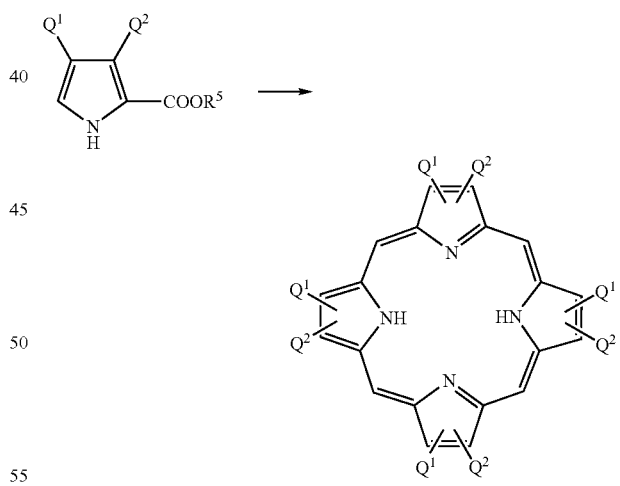

In the above formulae, $Q^1$ and $Q^2$ correspond to $Z^{ia}$ and $Z^{ib}$ in the formula (1) or (2), and $R^5$ is an alkyl group.

Among generalized porphyrin compounds of the present invention, a benzoporphyrin having a benzene ring condensed to at least one pyrrole ring, thiophene ring or furan ring, can be prepared by using as its precursor, the corresponding bicyclo compound. Such a precursor is not of a planar structure, and thus, it has a high solubility in a solvent and is hardly crystallizable and thus can be coated from a solution to present an amorphous or substantially amorphous good film. This film may be heat-treated for ethylene removal reaction to obtain a generalized benzoporphyrin film having a high planar nature. In the case of a non substituted non-metal structure, the reaction may be represented by the following chemical reaction. This reaction proceeds quantitatively by heating at a temperature of at least 100° C., preferably at least 150° C. Further, what is detached is an ethylene molecule, which will scarcely remain in the system, so that there will be no problem from the viewpoint of the toxicity or safety. Now, an example of a tetrabenzoporphyrin having four benzene rings condensed, will be shown.

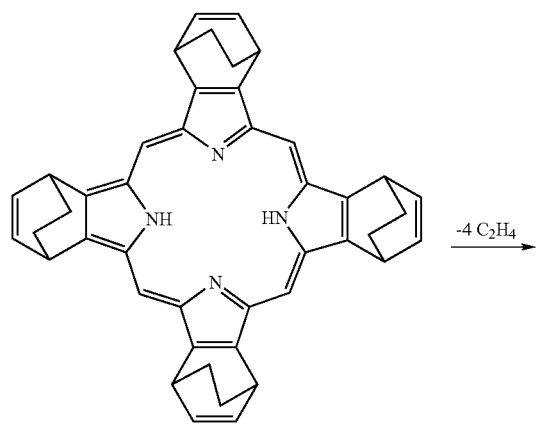

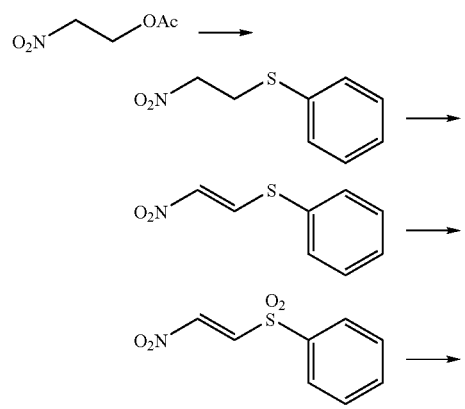

The following route may, for example, be mentioned as a synthesis of this bicyclo compound.

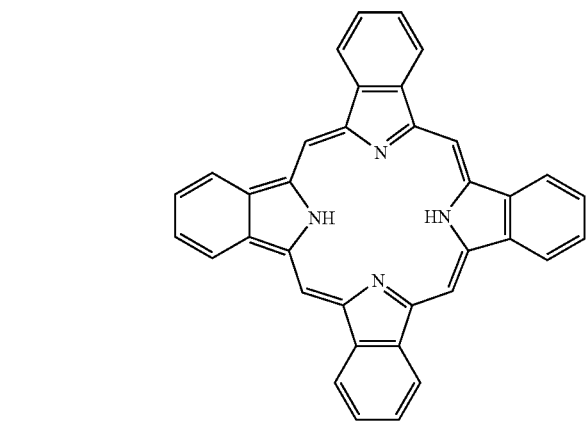

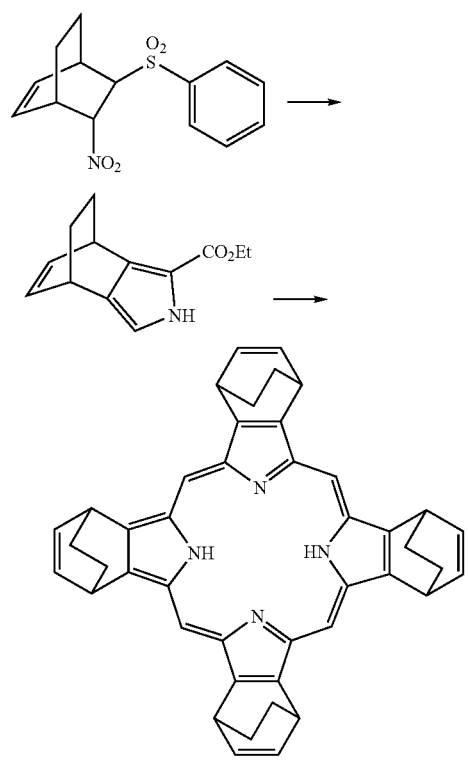

Here, the synthesis route up to the preparation of the pyrrole intermediate, may be replaced by another route, as follows.

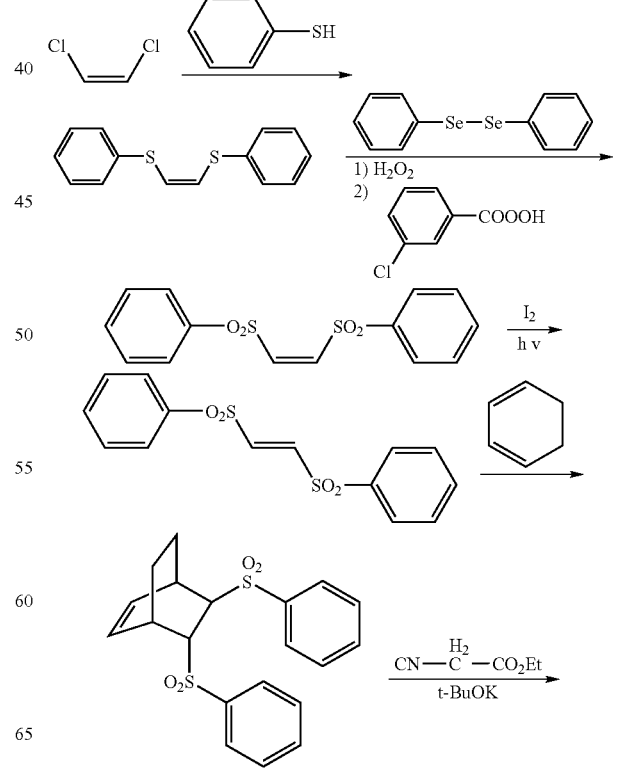

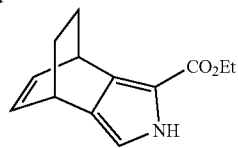

A metal complex of this precursor can be obtained by mixing this compound with a metal salt in an organic solvent capable of dissolving them. The metal salt may be any salt so long as it is soluble in the organic solvent, but an acetate is a typical example. The solvent may be any solvent so long as it is capable of dissolving the metal salt and the bicyclo compound, but a preferred example may be chloroform, an alcohol, dimethylformamide, tetrahydrofuran, acetonitrile, N-methylpyrrolidone, or a solvent mixture thereof.

Types of Devices
(1) Definition of Electronic Device

The electronic device of the present invention is a device having at least two electrodes and designed to control the electric current flowing between the electrodes or the resulting voltage by other than light, for example by electricity, magnetism or chemical substance. It may, for example, be a device for controlling an electric current or voltage by an application of a voltage, a device for controlling a voltage or electric current by an application of a magnetic field, or a device for controlling a voltage or electric current by the action of a chemical substance. Such control may, for example, be rectification, switching, amplification or oscillation. The corresponding devices presently practically realized by silicon or the like, include a resistor, a rectifier (a diode), a switching device (a transistor or a thyristor), an amplification device (a transistor), a memory device, a chemical sensor, and a combination of these devices, and an integrated device. The generalized porphyrin compound of the present invention has a high carrier mobility μ, whereby it is highly effective when applied to a switching device (a transistor or a thyristor).

Further, even a device to be controlled by light or to control emission of light may be included for an application other than an operation in which the generalized porphyrin material directly absorbs light or emits light, for example a device to be used for wiring or for control of the above voltage or electric current.

More specific examples of the electronic device may be those disclosed in Physics of Semiconductor Devices, 2nd Edition (Wiley-Interscience 1981) edited by S. M. Sze.

(2) Field Effect Transistor

As an example of an organic device of the present invention, a field effect transistor (FET) may be mentioned. This comprises two electrodes (a source electrode and a drain electrode) in contact with the semiconductor, and an electric current flowing between the electrodes (so-called a channel), is controlled by a voltage applied to another electrode so called a gate. The gate electrode is constructed merely to apply an electric field to the semiconductor layer, whereby an electric current will not basically flow, and it is called a field effect transistor.

According to the present invention, the organic semiconductor material is employed, and accordingly, it can be prepared by a process at a relatively low temperature, whereby a plastic film may be used as the subs-rate, and there is a merit in that a device which is light in weight, excellent in flexibility and scarcely breakable, can be prepared. Thus, it is possible to produce a field effect transistor having a thin film and being flexible, and such a transistor is used for a switching device for each cell, whereby an active matrix liquid crystal display having flexibility can be prepared, and thus it is widely applicable.

The operation characteristics of the field effect transistor are determined by e.g. the carrier mobility μ, the electroconductivity σ of the semiconductor layer, the capacitance Ci of the insulating layer, the structure of the device (the distance L and the width W between the source and drain electrodes, the thickness d of the insulating layer). As the semiconductor material to be used for the field effect transistor, the higher the carrier mobility μ, the better. However, the generalized porphyrin compound of the present invention has a characteristic that the carrier mobility μ is high, whereby when it is used for the field effect transistor, it is highly effective. Further, the field effect transistor of the present invention has a small leak current, and the ON/OFF ratio is large, whereby there is a merit that the stability of the film and the properties is high, and the useful life is long. Further, there are merits such that the useful temperature width is wide, the film forming property is good, it can be applicable to a large area, and it can be produced at low cost.

It is common to employ a structure wherein the gate electrode is insulated by an insulating film (Metal-Insulator-Semiconductor i.e. MIS structure). Further, there is a structure wherein a gate electrode is formed via a Schottkey barrier. However, in the case of FET employing an organic semiconductor material, the MIS structure is commonly employed.

Now, the field effect transistor of the present invention will be described in further detail with reference to the drawings, but the present invention is by no means restricted to such structures.

In FIGS. 1A to 1D, some structural examples of the field effect transistor device are shown. Reference numeral 1 represents a semiconductor layer, 2 an insulator layer, 3 and 4 a source electrode and a drain electrode, 5 a gate electrode, and 6 a substrate. The disposition of the respective layers and electrodes can be suitably selected depending upon the application of the device. As the electric current flows in a direction parallel to the substrate, the device is called a horizontal FET.

The substrate 6 is required to be such that each layer formed thereon can be maintained without peeling. As such a material, an insulating material, such as a sheet or film made of a resin, paper, glass or ceramics, one having an insulating layer formed by coating or the like on a conductive substrate made of a metal or an alloy, a composite material made of a combination of various types such as a resin and an inorganic material, may, for example, be mentioned. It is preferred to employ a resin film or paper, since flexibility can be imparted to the device.

A material having an electrical conductivity is used for the electrodes 3, 4 and 5. For example, a metal such as platinum, gold, aluminum, chromium, nickel, cobalt, copper, titanium, magnesium, calcium, barium or sodium, or an alloy containing them, an electroconductive oxide such as $InO_2$, $SnO_2$ or ITO, an electroconductive polymer compound such as polyaniline, polypyrrole, polythiophene, polyacetylene or polydiacetylene, a semiconductor such as silicon, germanium or gallium arsenide, or carbon material such as carbon black, fullerene, carbon nanotube or graphite, may, for example, be mentioned. Further, doping may be applied to the electroconductive polymer compound or to a semiconductor. The dopant may, for example, be an acid such as hydrochloric acid, sulfuric acid or sulfonic acid, a Lewis acid such as $PF_6$, $AsF_5$ or $FeCl_3$, a halogen atom such as iodine, or a metal atom such as sodium or potassium. Further, a conductive composite material having carbon black or metal particles dispersed to the above material, may also be employed.

Further, to the electrodes 3, 4 and 5, wirings not shown, are connected, and such wirings may be made of substantially the same materials as the electrodes.

For the insulating layer 2, a material having an insulating property can be employed. For example, a polymer such as polymethyl methacrylate, polystyrene, polyvinylphenol, polyimide, polycarbonate, polyester, polyvinyl alcohol, polyvinyl acetate, polyurethane, polysulfone, an epoxy resin or a phenol resin, a copolymer prepared by a combination thereof, an oxide such as silicon dioxide, aluminum oxide or titanium oxide, a ferroelectric oxide such as $SrTiO_3$ or $BaTiO_3$, a nitride such as silicon nitride, a dielectric such as a sulfide or fluoride, or a polymer having such dielectric particles dispersed therein, may be mentioned.

As mentioned above, the thickness of the insulating layer 2 is preferably as thin as possible within a range where the necessary functions can be obtained. Usually, the thickness is at least 1 nm, preferably at least 5 nm, more preferably at least 10 nm. However, usually, the thickness is at most 10 µm, preferably at most 1 µm, more preferably at most 500 nm.

With respect to the material of the semiconductor layer 1, a semiconductor layer containing the above-mentioned generalized porphyrin compound as the main component, is preferably employed. The main component means that it is contained in an amount of at least 50 wt %. More preferably, it is contained at least 80 wt %. In order to improve the properties or to impart other properties, other organic semiconductor materials may be mixed, or various additives may be added, as the case requires. Further, the semiconductor layer 1 may be composed of a plurality of layers.

The thickness of the semiconductor layer 1 is preferably as thin as possible within a range where the necessary functions can be obtained. In a horizontal field effect transistor device (a source electrode and a drain electrode as disposed substantially horizontally) as shown in FIG. 1, the characteristics of the device are not dependent on the film thickness so long as the film thickness is at least a prescribed level. On the other hand, if the film thickness becomes thick, a leak current tends to increase. In order to obtain the necessary functions, the film thickness is usually at least 1 nm, preferably at least 5 nm, more preferably at least 10 nm. However, the film thickness is usually at most 10 µm, preferably at most 1 µm, more preferably at most 500 nm.

In an organic electronic device of the present invention, between the respective layers, or on the outer surface of the device, another layer may be provided, as the case requires. For example, a protective layer may be formed on the semiconductor layer directly or via another layer, whereby there will be a merit such that the influence of the outer atmosphere such as moisture can be minimized. Further, there is a merit that the electrical characteristics can be stabilized, such that the ON/OFF ratio of the device is increased.

The material for the protective layer is not particularly limited. For example, films made of various resins such as an epoxy resin, an acrylic resin such as polymethyl methacrylate, polyurethane, polyimide, polyvinyl alcohol, a fluorinated resin and polyolefin, or films made of dielectrics, such as inorganic oxide films or nitride films, of e.g. silicon oxide, aluminum oxide, or silicon nitride, may preferably be mentioned. Particularly, a resin (polymer) having low water absorptivity or low permeability of oxygen or moisture, is preferred.

Some of generalized porphyrin compounds may absorb light to generate an electric charge. If necessary, the electronic device portion may be shielded from light, for example, by forming a pattern (a so-called black matrix) having a low light transmittance at a desired region. For such a pattern, a film of a m wherein said generalized porphyrin compound is a compound which has a porphyrin skeleton and which has a molecular structure such that the distance from the porphyrin ring plane to the center of each atom forming the porphyrin skeleton, is not more than 1 A.etal such as chromium, aluminum, silver or gold, a resin film having a pigment such as carbon black dispersed therein, or a film of an organic dye, may, for example, be used.

(3) Static Induction Transistor (SIT)

A static induction transistor (SIT) may be mentioned as one type of the field effect transistor. The structure of SIT will be described.

In horizontal FET, a source electrode and a drain electrode are disposed on a substrate, and the current flowing direction is perpendicular to the electric field induced by the gate. Whereas, SIT is characterized in that at a proper position between a source electrode and a drain electrode, a gate electrode is disposed in a grid pattern, and the current flowing direction is in parallel with the electric field induced by the gate.

Figure 2:
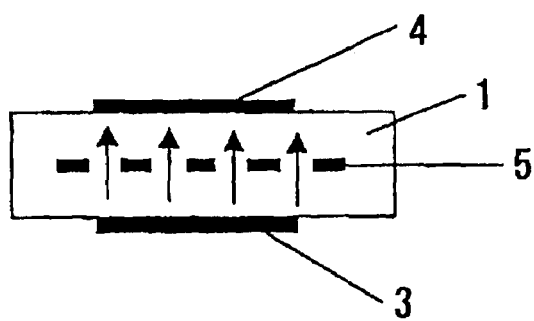
FIG. 2 is a schematic view showing a static induction transistor (SIT) of the present invention.

FIG. 2 is a schematic view showing a static induction transistor (SIT). Reference numeral 7 represents a source electrode, 8 a drain electrode, 9 a gate electrode, and 10 a semiconductor layer. These are formed on a substrate not shown. According to this SIT structure, the flow of carriers will spread in a plane, whereby a large amount of carriers can be moved all at once. Further, the source electrode and the drain electrode are arranged vertically, whereby the electrode spacing can be minimized, and the response speed will be high. Accordingly, this structure can be preferably applied to an application where a large current is conducted or switching is carried out at a high speed.

With respect to the semiconductor layer 10, the same description as of the above semiconductor layer 1 applies, and with respect to the electrodes 7 and 8, the same description as of the above electrodes 3, 4 and 5 applies.

The gate electrode 9 has a network or stripe structure, so that carriers will pass through spacings of the network or stripe structure. The spacings of the network of the gate electrode are preferably smaller than the distance between the source and the drain (which corresponds to the thickness of the device). Further, the thickness of the electrode is usually at least 10 nm, preferably at least 20 nm. However, it is usually at most 10 µm, preferably at most 1 µm.

As the material for the gate electrode 9, the same material as for the above-mentioned electrodes 3, 4 and 5 may be employed. However, preferably, an insular structured thin film made of a conductive material such as a metal, alloy or conductive polymer, is employed. For example, a semitransparent aluminum electrode in the form of a thin film having a thickness of at most 50 nm may be employed.

Between the gate electrode 9 and the semiconductor layer 10., it is common to provide an insulating layer or an energy barrier to prevent outgoing or incoming of carriers to or from the electrode. For example, an insulating layer may be formed by patterning around the electrode. Otherwise, as the electrode material, a metal capable of forming an energy barrier against a semiconductor may be selected to suppress outgoing or incoming of carriers to or from the semiconductor layer. For example, by selecting aluminum, a so-called shotkey barrier can be formed against a p-type semiconductor.

Further, between the respective layers or on the outer surface of the device, another layer may be formed as the case requires.

The static induction transistor of the present invention has such merits that the carrier mobility μ is high, the leak current is small, the ON/OFF ratio is large, the stability of the film and the properties is high, and the useful life is long. Further, it has such merits that the useful temperature range is wide, the film forming property is good, it is applicable to a large area, and it can be produced at low cost.

(4) Diode Device

Figure 3E:
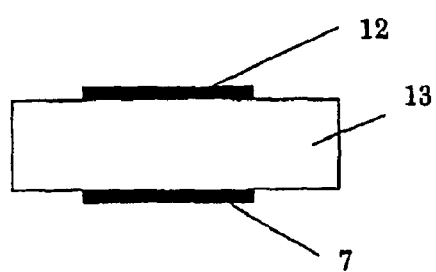
FIGS. 3E and 3F are schematic views showing diode devices of the present invention.
Figure 3F:
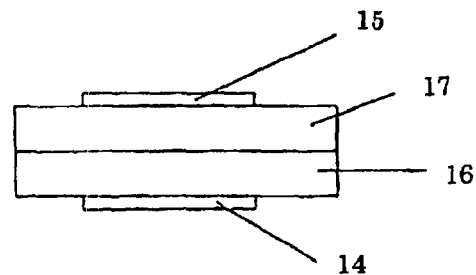

As another example, a diode device may be mentioned. This is a two-terminal device having an asymmetrical structure. FIGS. 3E and 3F are schematic views of diode devices. These devices are provided on substrates not shown.

The device of 3E has a structure wherein a semiconductor layer 13 comprising the generalized porphyrin compound is sandwiched between two metal electrodes 11 and 12 having different work functions. With respect to the semiconductor layer 13, the same description as of the above semiconductor layer 1 applies. At least one of the electrodes 11 and 12 forms an energy barrier against the semiconductor material. To form the energy barrier, the electrodes and the semiconductor may be selected to have different work functions. For example, as a metal to form an energy barrier against the p-type semiconductor, aluminum is often used. As other electrode materials, the same ones as for the above-described electrodes 3, 4 and 5 may be employed, but preferred is a metal or an alloy. When a voltage is applied to this device, so-called rectification will be observed, wherein the flowing current value varies depending upon the polarity of the voltage. Accordingly, as an application of such a diode device, a rectification device may be mentioned.

Whereas, the device shown in FIG. 3F has a structure in which semiconductor layers 16 and 17 having substantially different work functions, are sandwiched between electrodes 14 and 15. With respect to the semiconductor layer 16, the same description as of the above semiconductor layer 1 applies. The semiconductor layer 17 may be made of any material so long as its work function is substantially different from the semiconductor layer 16, and as such a material, a perylene pigment, a phthalocyanine material, fullerene or a conjugated polymer, may, for example, be mentioned. With respect to the electrodes 14 and 15, they may be made of the same material or different materials. The same materials as for the above electrodes 3, 4 and 5 may be employed.

Further, between the respective layers or on the outer surface of the device, another layer may be provided as the case requires.

(5) Resistance, Etc.

Further, as another application, a resistant element may be mentioned. This is a two-terminal element having a symmetrical structure in which a semiconductor layer formed on a substrate is sandwiched between two electrodes. The resistant element may be used as a resistor to adjust the resistance between the electrodes, or as a capacitor to adjust the capacitance between the electrodes by increasing the resistance.

With respect to the semiconductor layer, the same description as of the above semiconductor layer 1 applies, and with respect to the electrodes, the same description as of the above electrodes 3, 4 and 5 applies.

Further, between the respective layers or on the outer surface of the element, another layer may be provided, as the case requires.

Such a diode device or the resistance element will have a merit such that by using the organic semiconductor material of the present invention showing a high carrier mobility, the device parameter such as the resistance value can be controlled widely, such is advantageous for integration.

(6) Application of the Organic Electronic Device of the Present Invention (6-1) Active Matrix The organic electronic device of the present invention can be used as a switching device of an active matrix of a display. Namely, by utilizing the ability to switch the electric current between the source and the drain by the voltage applied to the gate, the switch is put on only when a voltage is applied or a current is supplied to a display device, and during other time, the circuit is open, thereby to carry out high speed high contrast display.

As a display device to which the present invention is applicable, a liquid display device, a polymer-dispersed type liquid crystal display device, an electrophoretic display device, an electroluminescent devices or an electrocromic device may, for example, be mentioned.

Particularly, with the organic electronic device of the present invention, preparation of the device by a low temperature process is possible, and it is possible to employ a substrate which is not durable against high temperature treatment, such as a plastic plate, a plastic film or paper. Further, preparation of the device by a coating or printing process is possible, it is suitable for application to a display having a large area. Further, it is advantageous as a device which makes an energy saving process or a low cost process possible, or as a substitute for a conventional active matrix.

(6-2) IC

Further, by integrating a transistor, a digital device or an analogue device can be realized. As such an example, a logical circuit such as AND, OR, NAND or NOT, a memory device, an oscillation device or an amplification device may, for example, be mentioned. Further, by a combination thereof, an IC card or an IC tag may be prepared.

(6-3) Sensor

An organic semiconductor undergoes a substantial change in its properties by an external stimulus such as a gas a chemical substance or a temperature, and its application to a sensor is conceivable. For example, by measuring the amount of change in the properties of the organic electronic device of the present invention by its contact with a gas or a liquid, it is possible to detect chemical substances contained therein quantitatively or qualitatively.

Process for Producing the Organic Electronic Device of the Present Invention

A preferred process for producing the organic electronic device of the present invention will be described with reference to a case of the field effect transistor (FET) shown in FIG. 1A, but such a process is likewise applicable to other organic electronic devices.

(1) Substrate and Treatment of the Substrate

In general, an organic electronic device such as a field effect transistor is prepared by providing a necessary layer and electrodes on a substrate 1. As the substrate, one described above can be employed.

In some cases, it is possible to improve the properties of the device by applying a prescribed surface treatment to the substrate. For example, by adjusting the degree of hydrophilicity/hydrophobicity of the substrate surface, the quality of the film to be formed thereon can be improved. Especially, the properties of the organic semiconductor material will change substantially by the state of the film such as alignment of molecules, and by surface treatment of the substrate, it is considered possible to control the molecular alignment at the interfacial portion between the substrate and the semiconductor film to be formed thereon, thereby to improve the properties.

Such treatment of the substrate may, for example, be hydrophobic treatment with e.g. hexamethyldisilazane, cyclohexene or octadecyl trichlorosilane, acid treatment with e.g. hydrochloric acid, sulfuric acid or acetic acid, alkali treatment with e.g. sodium hydroxide, potassium hydroxide, calcium hydroxide or ammonia, ozone treatment, fluorination treatment, plasma treatment in e.g. oxygen or argon, treatment for forming a Langmuir Blodgett film, treatment for forming a thin film of other insulator or semiconductor, mechanical treatment, or electric treatment such as corona discharge treatment.

(2) Formation of Electrodes

Then, a gate electrode 5 is formed. As the electrode material, the one described above can be employed.

To form an electrode film, known various methods may be employed, such as a vacuum vapor deposition method, a sputtering method, a coating method, a printing method and a sol gel method.

After the film formation, patterning is carried out, as the case requires to obtain a desired shape. Also for such patterning, known various methods may be employed. For example, a photolithography method in which patterning and etching (wet etching with an etching liquid, or dry etching by reactive plasma) of a photoresist are combined, a printing method such as ink jet printing, screen printing, offset printing or relief printing, a soft lithography method such as a microcontact printing method, and a method having a plurality of such methods combined, may be used. Further, a pattern may directly be prepared, for example, by irradiating energy rays such as laser or electron rays to remove the material or to change the electroconductivity of the material.

(3) Insulating Layer

Then, an insulator layer 2 is formed. As the insulator material, the one described in the above (3) can be employed.

To form the insulator layer 2, known various methods may be employed. For example, a coating method such as spin coating or blade coating, a printing method such as screen printing or ink jet printing, a vacuum vapor deposition method, a sputtering method, or a method of forming an oxide film on a metal, such as alumite on aluminum, may be employed.

In an embodiment wherein a semiconductor layer is formed on an insulator layer, a prescribed surface treatment may be applied to the insulator layer in order to have semiconductor molecules well aligned at the interface of the two layers. The method for the surface treatment may be the same as used for the surface treatment of the substrate.

Further, a source electrode 3 and a drain electrode 4 are formed, but the forming method, etc. may be in accordance with those for the gate electrode 5.

(4) Semiconductor Layer

Then, an organic semiconductor layer 1 is formed. As the organic semiconductor material, the one described above can be employed. To form the semiconductor layer, known various methods may be employed. However, they may be generally classified into a method for forming by a vacuum process such as a sputtering method or a vapor deposition method, and a method for forming by a solution process, such as a coating method or a printing method.

(5) Vacuum Process

A method of forming an organic semiconductor material into a film by a vacuum process to obtain an organic semiconductor layer, will be described in detail. For example, a vacuum vapor deposition method may be employed wherein the material is put into a crucible or a metal boat and heated in vacuum to evaporate it and to let it deposit on the substrate. At that time, the vacuum degree is usually at most $1\times10^{-3}$ Torr ($1.3\times10^{-1}$ Pa), preferably at most $1\times10^{-6}$ Torr ($1.3\times10^{-4}$ Pa). Further, depending upon the substrate temperature, the properties of the semiconductor film, and accordingly, of the device, will change, and accordingly, the optimum substrate temperature is selected. It is usually within a range of from 0° C. to 200° C. Further, the vapor deposition rate is usually at least 0.001 nm/sec, preferably at least 0.01 nm/sec. However, it is usually at most 10 nm/sec, preferably at most 1 nm/sec. Instead of the method of heating and evaporating the material, a sputtering method may be employed wherein accelerated ions of e.g. argon are impinged to the material target to drive out the material atoms and to let them deposit on the substrate.

The organic semiconductor material of the present invention is a relatively low molecular compound. Accordingly, such a vacuum process can be employed. The vacuum process requires an expensive installation but has a merit such that the film forming performance is good, and a uniform film can readily be obtained.

(6) Solution Process

A method of forming an organic semiconductor material into a film by a solution process thereby to obtain an organic semiconductor layer, will be described in detail. Firstly, the organic semiconductor material is dissolved in a solvent and coated on a substrate. As the coating method, a coating method such as casting wherein the solution is simply dropped, spin coating, dip coating, blade coating, wire bar coating or spray coating, a printing method such as ink jet printing, screen printing, offset printing or relief printing, a soft lithography method such as a microcontact printing method, or a method having a plurality of such methods combined, may be employed. Further, as a technique similar to the coating, a Langmuir Blodgett method wherein a monomolecular film formed on a water surface is transferred to and laminated on a substrate, or a method of interposing liquid crystal or molten liquid between a pair of substrates or introducing it between the substrates by a capillary phenomenon, may, for example, be mentioned.

It is advantageous to use the solution process in that an organic electronic device having a large area can readily be prepared by a relatively inexpensive installation.

A device may also be prepared by dissolving the generalized porphyrin compound of the present invention in a solvent, followed by coating. In such a case, the generalized porphyrin compound to be finally used in the device, may directly be coated, but it is also possible to have a highly soluble compound (hereinafter referred to as a precursor) coated and finally converted to a generalized porphyrin compound by the change of its chemical structure. This is particularly useful to form the material hardly soluble in a solvent into a film by a coating method.

As such a precursor, one having the following bicyclo structure may be mentioned as a preferred example.

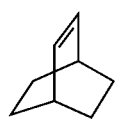

This bicyclo structure changes into a benzene ring by dissociation of the ethylene molecule by heating.

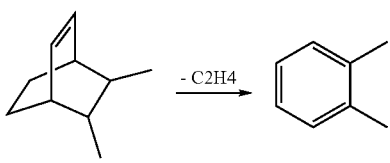

The bicyclo structure is sterically bulky and thus is poor in crystallizability. Molecules having this structure have good solubility, and have, in many cases, such a nature that when coated from their solution, a low crystalline or amorphous film can readily be obtained. When it changes into a benzene ring by the heating step, it will have a molecular structure having a good planar nature, and thus it changes into molecules having good crystallizability. Accordingly, by utilizing the chemical change from such a precursor, it is possible to obtain a film having a good crystallinity by coating. This heating step may also have another purpose such as to distill off the coating solvent.

Particularly, among generalized porphyrin compounds of the present invention, a compound so-called a benzoporphyrin, having a benzene ring condensed to a pyrrole ring, a thiophene ring or a furan ring, can be obtained from one having a bicyclo structure as the precursor, and as such, it is advantageous to obtain a device by coating.

Further, by the solution process, the semiconductor layer may be made thick by repeating the coating and drying steps as many times as required. In a case where a semiconductor film is formed by conversion from a precursor, it is possible to form a thick film by lamination by utilizing the difference in solubility between the precursor and the semiconductor by repeating the coating and conversion to semiconductor steps.

Further, different film forming methods such as coating and vapor deposition, may be used in combination, or different materials may be laminated by the same or different film forming methods.

In general, it is considered that by the solution process, the film-forming performance is not high, and it is difficult to obtain a highly crystalline organic semiconductor film. However, according to this method, a highly crystalline organic semiconductor film having good properties can be obtained by a simple solution process, such being very desirable. The film thus formed has a high carrier mobility and has desirable characteristics such that the leak current is small, and the ON/OFF ratio is high. This method is an excellent method which is applicable not only to the organic semiconductor material of the present invention, but widely to organic semiconductor materials in general.

(7) Post Treatment of the Semiconductor Layer

The organic semiconductor layer thus prepared may be subjected to post treatment to further improve the characteristics. For example, by heat treatment, it is possible to relax a strain in the film formed during the film formation, whereby it is possible to improve the properties or stability. Further, by exposing it to an oxidizing or reducing gas or liquid, such as oxygen or hydrogen, the property change by oxidation or reduction may be induced. This may be utilized, for example, for the purpose of increasing or decreasing the carrier density in the film.

(8) Doping Treatment

Further, by adding a trace amount of an element, an atomic group, a molecule or a polymer by doping, it is possible to have the properties changed to be desirable. For example, oxygen, hydrogen, an acid such as hydrochloric acid, sulfuric acid or sulfonic acid, a Lewis acid such as $PF_6$, $AsF_5$ or $FeCl_3$, a halogen atom such as iodine, or a metal atom such as sodium or potassium, may, for example, be doped. This can be accomplished by contacting the semiconductor layer with such a gas, by dipping it in a solution, or by subjecting it to electrochemical doping treatment. Such doping may be carried out not only after forming the film but also by an addition during the preparation of the material, or in the production process from a solution, by an addition to the solution or by an addition to the stage of a precursor film. Further, it is also possible to carry out doping by co-vapor depositing the material to be added during the vapor deposition, by mixing the dopant to the atmosphere during the film formation, or by accelerating ions in vacuum to impinge them to the film.

The effects of such doping may, for example, be a change in the electroconductivity due to an increase or decrease of the carrier density, a change in the polarity of the carrier (p-type, n-type), a change in the Fermi level, etc., and they are commonly used in semiconductor devices. Doping treatment can be likewise utilized for the organic electronic device of the present invention.

(9) Protective Layer

In the organic electronic device of the present invention, between the respective layers or on the outer surface of the device, another layer may be provided as the case requires. For example, a protective layer may be formed on the semiconductor layer directly or via another layer, whereby the influence of the external atmosphere can be minimized. Further, there is another merit that the electrical characteristics of the device can be stabilized. As the material for the protective layer, the one described above may be employed.

To form the protective layer, known various methods may be employed. However, in a case where the protective layer is made of a resin, a method of coating a resin solution, followed by drying to form a resin film, or a method of coating or vapor depositing a resin monomer, followed by polymerization, may, for example, be employed. It is also possible to carry out crosslinking treatment after the film formation. In a case where the protective layer is made of an inorganic substance, a forming method by a vacuum process such as a sputtering method or a vapor deposition method, or a forming method by a solution process represented by a sol gel method, may, for example, be employed.

Now, the present invention will be described in further detail with reference to Examples. However, it should be understood that the present invention is by no means restricted to such specific Examples.

PREPARATION EXAMPLE 1

A bicyclo compound (I) was prepared by the following synthesis route.

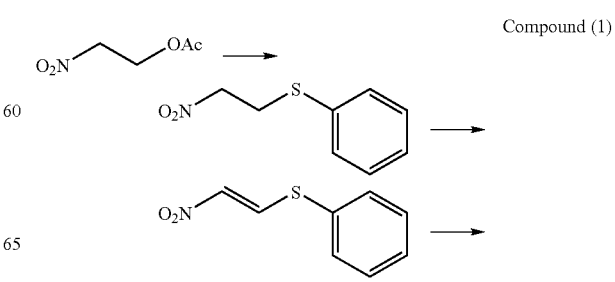

Compound (1)

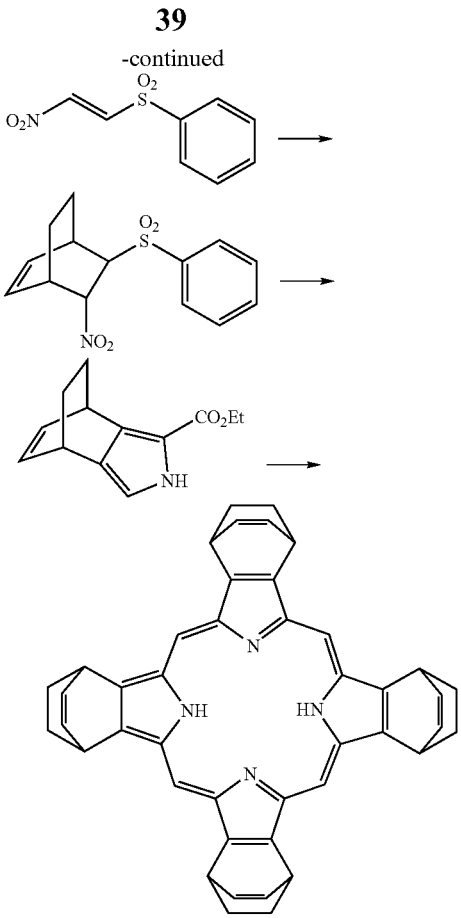

53.5 ml of thiophenol and 51.25 g of potassium hydroxide was dissolved in 600 ml of ethanol. To this solution, 19.4 ml of cis-1,2-dichloroethylene was slowly dropwise added. Then, the mixture was stirred at room temperature for 30 minutes and further heated and stirred at a temperature of from 80 to 90° C. for 23 hours. The solvent was concentrated under reduced pressure, and water was added thereto, followed by extraction with chloroform. The organic layer was washed with water and a saturated sodium chloride aqueous solution, dried over anhydrous sodium sulfate and concentrated under reduced pressure to obtain cis-1,2-phenylthioethylene.

This cis-1,2-phenylthioethylene and 750 mg of diphenyl diselenide were dissolved in 100 ml of methylene chloride. This solution was cooled in an ice bath, and 175 ml of a 30% hydrogen peroxide aqueous solution was slowly added thereto. The mixture was vigorously stirred at room temperature overnight, whereupon precipitated crystals were collected by filtration, dissolved in chloroform, then washed with water, a saturated sodium carbonate aqueous solution and a saturated sodium chloride aqueous solution, then dried over anhydrous sodium sulfate and concentrated under reduced pressure. Further, this product was dissolved in 500 ml of chloroform, and while cooling the solution in an ice bath, 84 g of m-chloroperbenzoate was slowly added, and the mixture was stirred at room temperature overnight. Precipitated solid was subjected to filtration by cerite, and the organic layer was washed with water, a saturated sodium carbonate aqueous solution and a saturated sodium chloride solution, dried over anhydrous sodium sulfate and then concentrated under reduced pressure. This solid was rinsed by ethyl ether to obtain 67.06 g of cis-1,2-diphenylsulfonylethylene (yield: 87%). Colorless crystal, mp: 100 to 101° C.

This cis-isomer and a catalytic amount of iodine were dissolved in methylene chloride, followed by irradiation with sunlight, whereupon precipitated solid was collected by filtration to obtain trans-1,2-diphenylsulfonylethylene. Colorless crystals, mp: 219.5° C.

29.33 g of trans-1,2-diphenylsulfonylethylene was dissolved in 200 ml of toluene, and then, 11.4 ml of 1,3-cyclohexadiene was added, followed by dry distillation for 21 hours and then by recrystallization to obtain 35.66 g (yield: 96.5%) of 5,6-diphenylsulfonyl-bicyclo-[2,2,2]oct-2-ene.

7.76 g of this compound was put into a reactor, and after flushing with nitrogen, 50 ml of anhydrous tetrahydrofuran (THF) was added and dissolved. 2.43 ml of ethyl cyanoacetate was added thereto, and the reaction solution was cooled in an ice bath, and 50 ml of a 1M solution of t-BuOK/THF was slowly dropwise added thereto. Thereafter, the reaction solution was returned to room temperature and stirred overnight. The reaction solution was quenched with 1N hydrochloric acid and extracted with chloroform, followed by washing with water and a saturated sodium chloride aqueous solution. Then, the organic layer was dried over anhydrous sodium sulfate, concentrated under reduced pressure and purified by silica gel chromatography to obtain 3.49 g (yield: 80.4%) of ethyl 4,7-dihydro-4,7-ethano-2H-isoindole-1-carboxylate. Colorless crystals, mp: 129-130° C.

0.109 g of the obtained crystals were dissolved in 15 ml of THF, and 0.144 g of LiAlH$_4$ was dropwise added thereto at 0° C. with stirring, followed by stirring at 0° C. for 2 hours. The reaction solution was injected into 25 ml of water and extracted three times with 50 ml of chloroform. The extracted solutions were put together, and 0.010 g of p-toluenesulfonic acid was added thereto, followed by stirring at room temperature for 12 hours. Then, 0.150 g of p-chloranil was added thereto, followed by stirring at room temperature for 12 hours. Then, the reaction solution was injected to water. The organic layer was separated and washed five times with 250 ml of an aqueous sodium hydrogencarbonate solution, once with 250 ml of water and 100 ml of a saturated sodium chloride aqueous solution, followed by drying over magnesium sulfate. The solvent was distilled off, and the residue was purified by column chromatography (chloroform, alumina) to obtain 0.094 g of the desired porphyrin compound (1) containing the bicyclo structure.

The main peak of m/Z=622 (M⁻) was observed by a negative ion mode of the MALDI-TOF mass spectrum.

Figure 4:
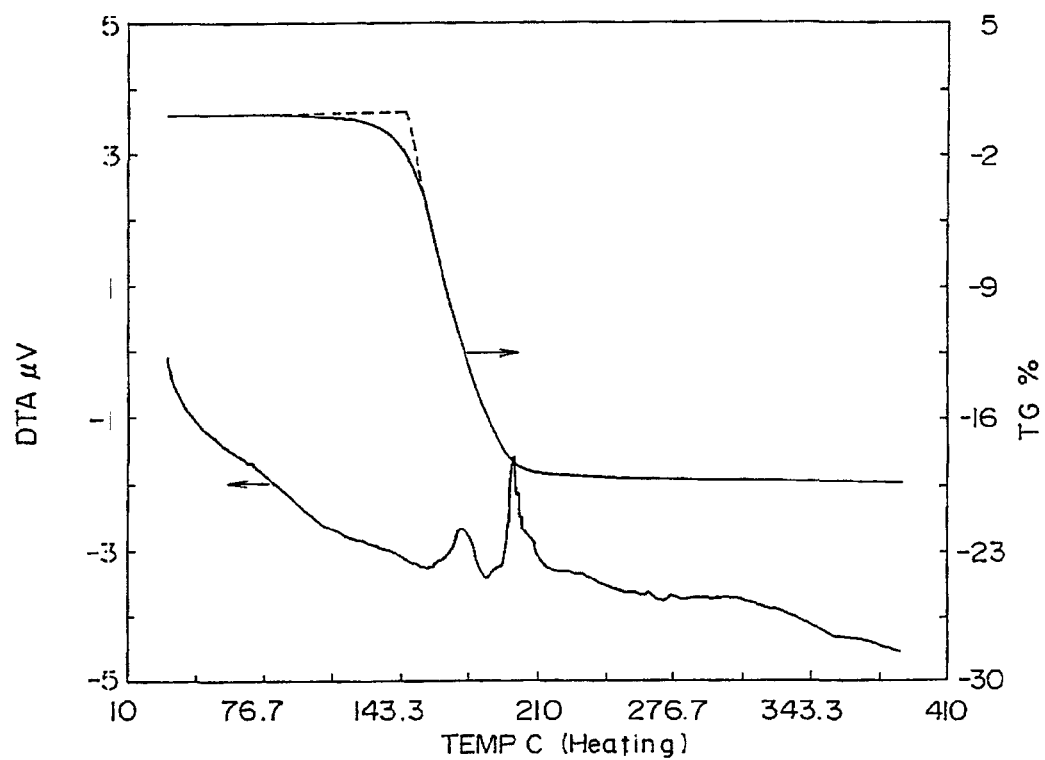
FIG. 4 is a graph showing the results of a thermal analysis of the porphyrin compound obtained in Preparation Example 1.

The results (DTA-TG) of the thermal analysis of this compound are shown in FIG. 4.

Within a temperature range of from 146° C. to 198° C., a decrease in weight and heat generation are observed. This weight reduction (about 18%) corresponds to detachment of four ethylene molecules from the bicyclo compound to the change into tetrabenzoporphyrin.

Figure 5:
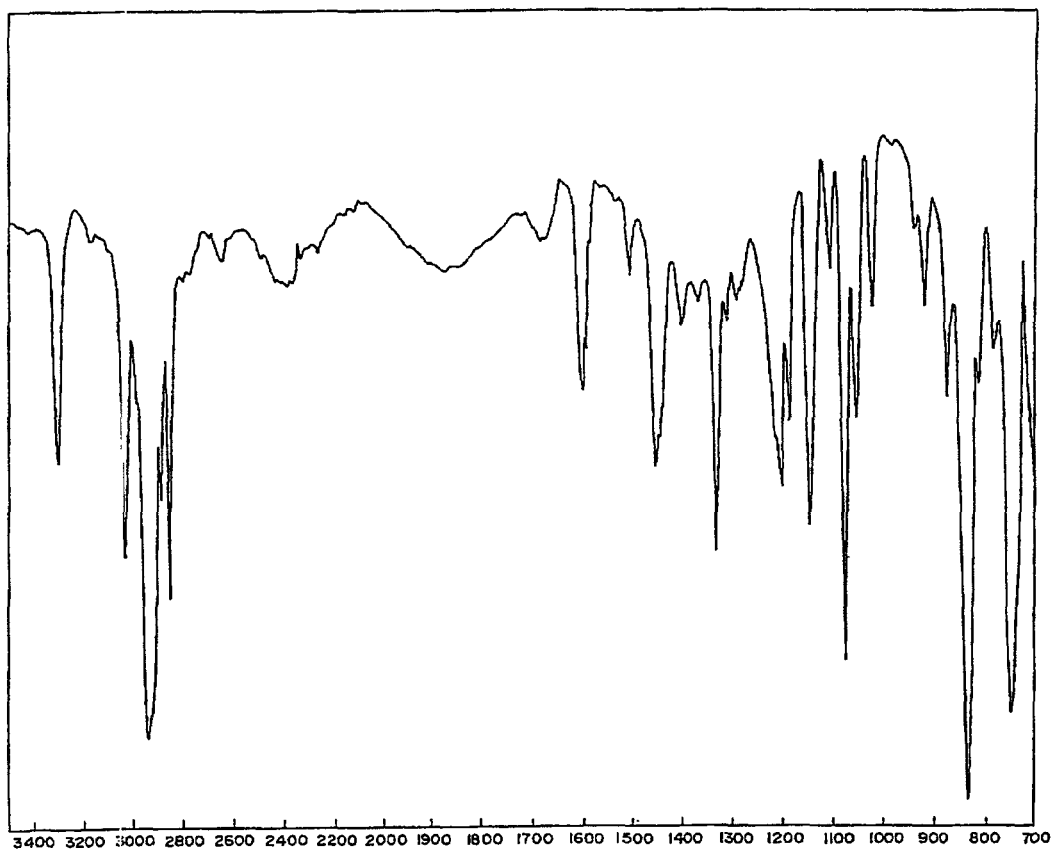
FIG. 5 is a graph showing the IR spectrum of a film obtained by drying a solution of the porphyrin compound (I) obtained in Preparation Example 1.
Figure 6:
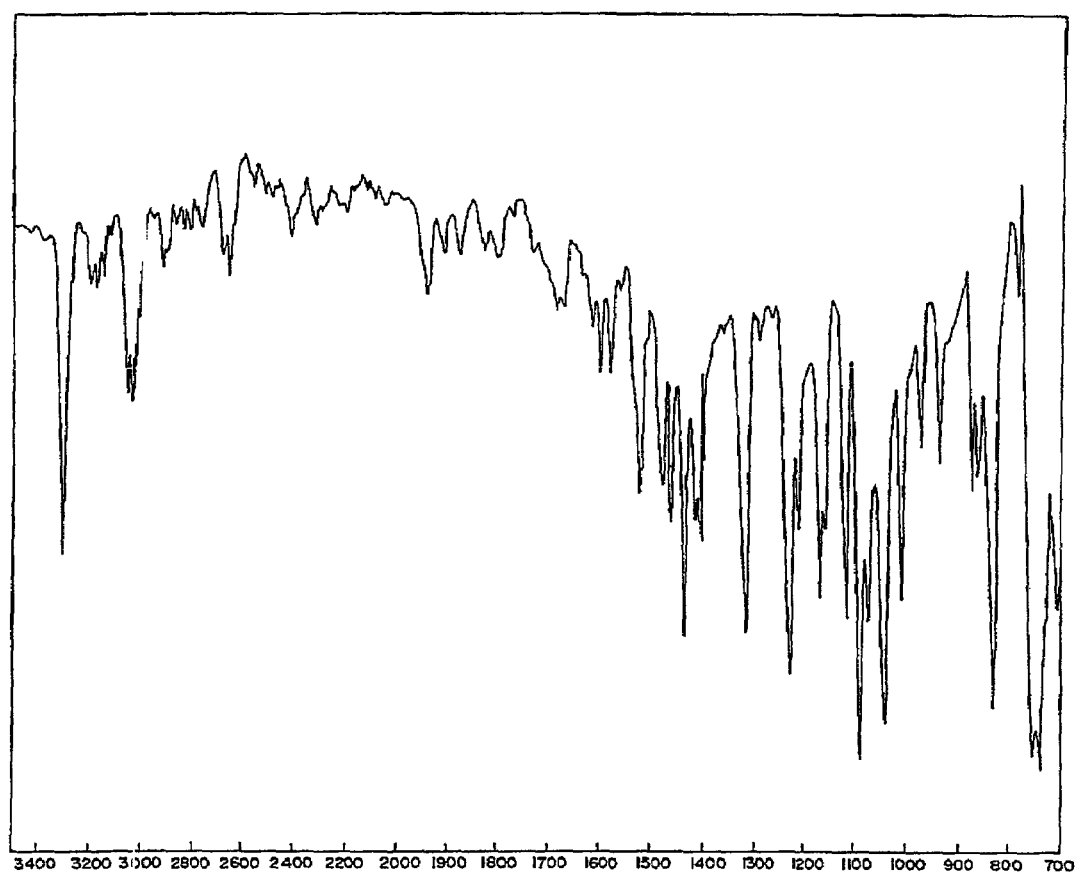
FIG. 6 is a graph showing the IR spectrum of a film obtained by further heating the film of FIG. 5 obtained in Preparation Example 1.

A chloroform solution of the porphyrin compound (I) was cropped on a gold-vapor deposited film, and the solvent was dried to form a film. The IR spectrum of the film is shown in FIG. 5. This film was heated at 210° C. for 2 minutes, and the IR spectrum of the film is shown in FIG. 6. A change of the IR spectrum reflecting the change in the molecular structure due to the detachment of the ethylene molecules, was observed, whereby it is evident that by the heating of the film, tetrabenzoporphyrin was formed.

The bicyclo compound (I) was heated at 210° C. for 10 minutes, and the mass spectrum thereof was measured by a negative ion mode in the same manner as for the bicyclo compound, by the MALDI-TOF method, whereby the molecular ion peak of tetrabenzoporphyrin of m/z=510 (M⁻) was observed, whereby the change into tetrabenzoporphyrin by heating was confirmed. Further, the IR spectrum of this heated one, substantially agreed to the IR spectrum after heating, as measured on the above substrate, whereby it was confirmed that one formed by the heating was tetrabenzoporphyrin.

Figure 7:
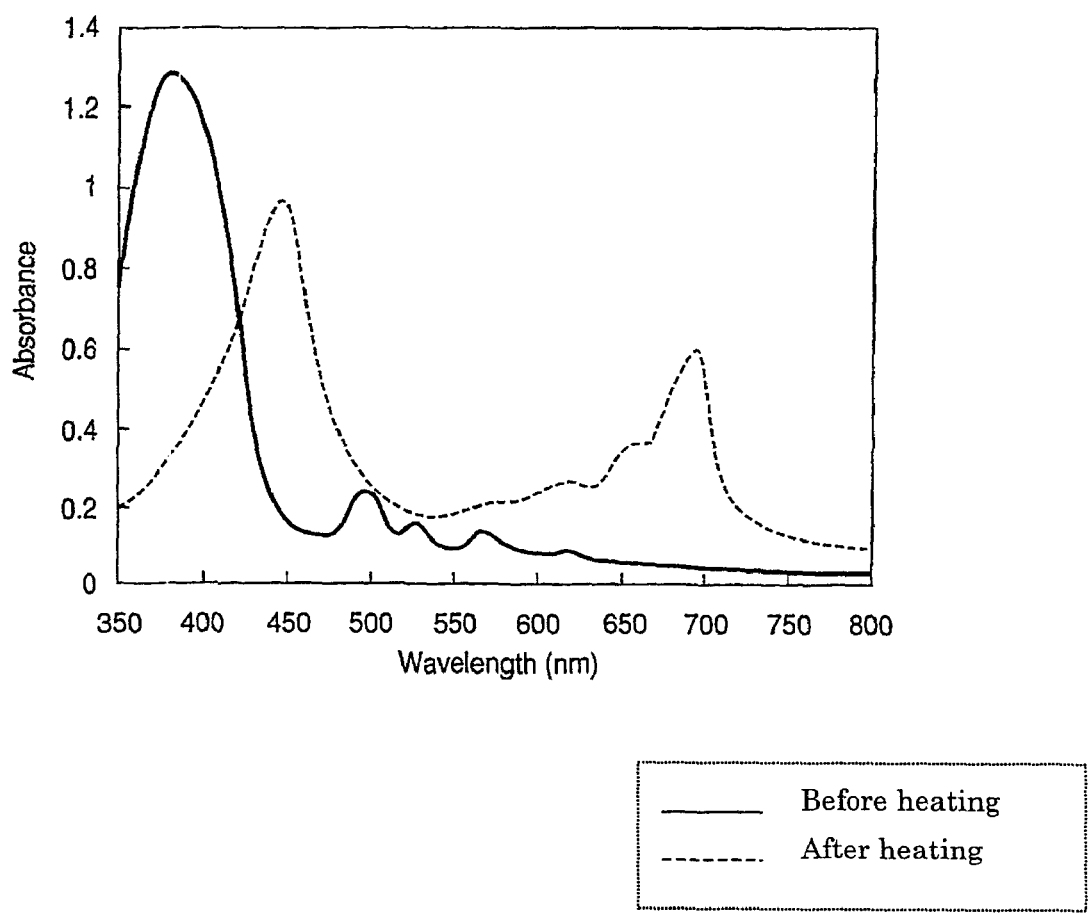
FIG. 7 is a graph showing the thin film absorption spectra before and after heating in Preparation Example 1.

The chloroform solution of the bicyclo compound (1) was spin-coated on a quartz glass substrate, and the solvent was dried to form a film. This film was heated at 213° C. for 10 minutes, and the comparison of the ultraviolet-visible light absorption spectra of the films before and after the heating, is shown in FIG. 7. In this Fig. the change from the bicyclo compound to the tetrabenzoporphyrin (690 nm) is observed as an increase in the intensity and a shift to a long wavelength side, of the Q band in the absorption spectrum of the porphyrin.

PREPARATION EXAMPLE 2

0.02 g of the bicyclo compound (1) of Preparation Example 1 and 0.1 g of zinc acetate dihydrate were put in a solvent mixture comprising 30 ml of chloroform and 3 ml of methanol, followed by stirring at room temperature for 3 hours. The reaction solution was washed twice with 100 ml of water and once with 40 ml of a saturated sodium chloride aqueous solution. The organic phase was dried over sodium sulfate. The solvent was distilled off, and the obtained solid was recrystallized from a solvent mixture of chloroform and methanol to obtain 0.022 g of a zinc complex of the bicyclo compound (1). Further, by gel permeation chromatography (Nippon Bunseki Kogyo JAIGEL-1H, 2H, chloroform), only the single peak was fractionated and purified.

The mass spectrum was measured, and the molecular peak was confirmed.

PREPARATION EXAMPLE 3

Preparation of 21,23-dithiaporphyrin 5

A dithiaporphyrin compound having the following bicyclo ring structure was prepared by the following sythesis route.

Here, the starting material diformylthiophene was prepared by the method reported in Tetrahedron Letters, vol. 43, 8485, (2002).

(1) Preparation of 1,3-bis-(dihydroxymethyl)-4,7-dihydro-4,7-ethano-2-benzo[c]thiophene 2

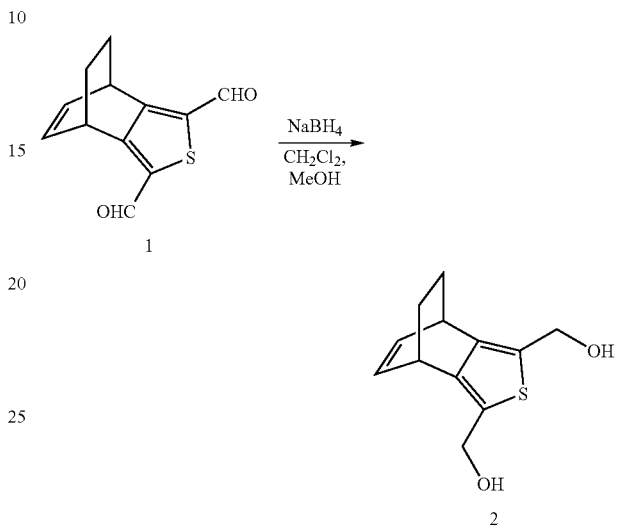

Into a 50 ml flask, diformylthiophene 1 (0.437 g, 2.0 mmol) was put and dissolved in 10 ml of dichloromethane and 10 ml of methanol. The flask was cooled to 0° C. and then, NaBH₄ (0.277 g, 6.0 mmol) was added, followed by stirring for 30 minutes. The reaction solution was quenched with water. Then, the organic layer was extracted with dichloromethane. The organic layer was washed with water and a saturated sodium chloride aqueous solution, then dried over sodium sulfate and concentrated. The obtained oil was crystallized in a refrigerator and then purified by recrystallization (CHCl₃/hexane) to obtain dihydroxymethylthiophene 2 as the desired product in a yield of 78%. Appearance: colorless crystals, mp: 143 to 145° C.

(2) Preparation Thiatripyran Diethyl Ester 3

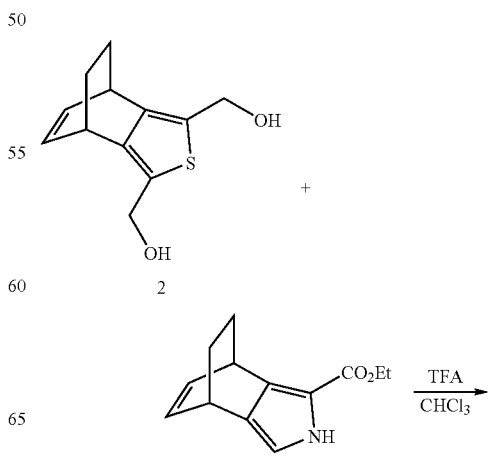

-continued

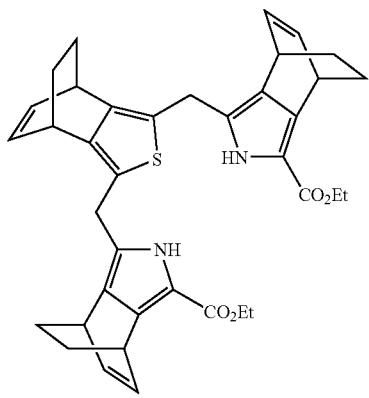

3

Into a 200 ml flask, dihydroxymethylthiophene 2 (0.888 g, 4.0 mmol) and bicyclopyrrole ethyl ester (1.737 g, 8.0 mmol) were put, and after flushing the interior of the Elask with argon, dissolved in 60 ml of chloroform. This flask was cooled to 0° C., and 1 ml of TFA was added, followed by stirring for 1 hour and then by refluxing for 5 hours. The reaction solution was poured into water and quenched. Then, the organic layer was extracted with chloroform. The organic layer was washed with water, an aqueous sodium bicarbonate solution and a saturated sodium chloride aqueous solution and then dried over sodium sulfate and concentrated. The obtained crude product was washed with a solvent mixture of ethyl ether and hexane and then purified by recrystallization (CHCl$_3$/hexane) to obtain thiatripyran diethyl ester 3 as the desired product in a yield of 90%. Appearance: slightly brown powder (containing steric isomers), mp: >180° C. (decomposed).

(3) Preparation of Thiatripyran Dicarboxylic Acid 4

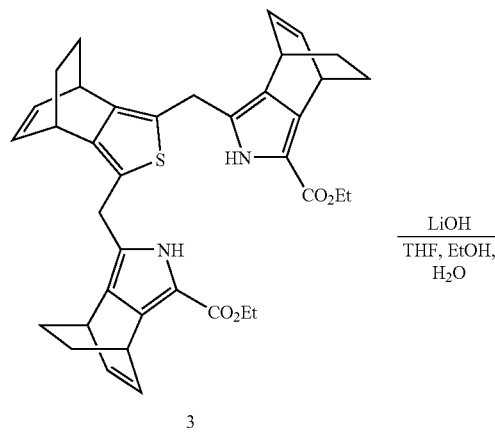

3

-continued

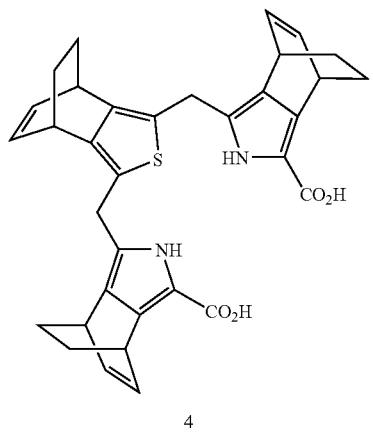

4

Into a 100 ml flask, thiatripyran diethyl ester 3 (0.620 g, 1.0 mmol) was put and dissolved in 10 ml of tetrahydrofuran (THF), 8 ml of ethanol and 12 ml of water. LiOH.H$_2$O (0.840 g, 20 mmol) was added, followed by refluxing for 20 hours. The reaction solution was cooled to room temperature, and a 1N HCl aqueous solution was slowly added, and the pH of the solution was adjusted to 1. Then, the organic layer was extracted with ethyl acetate. The organic layer was washed with water and a saturated sodium chloride aqueous solution, then dried over sodium sulfate and concentrated. The obtained crude product was washed with a solvent mixture of ethyl ether and hexane to obtan thiatripyran dicarboxylic acid as the desired product in a yield of 98%. This product was used for the next reaction without purification. Appearance: slight brown powder (containing steric isomers).

(4) Preparation of 21,23-dithiaporphyrin 5

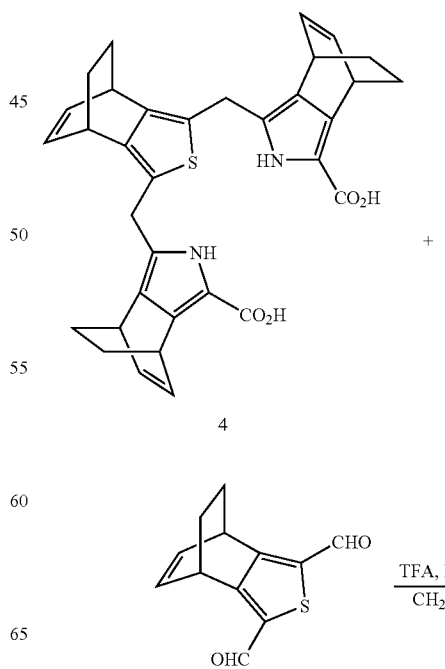

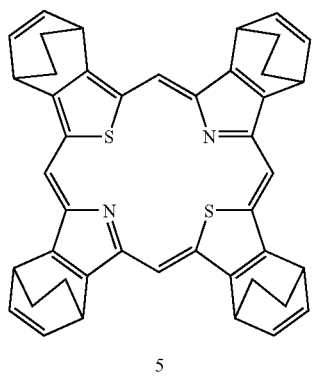

5

Into a light-shielded 500 ml flask, thiatripyran dicarboxylic acid 4 (0.508 g, 0.9 mmol) was put, and after flushing the interior with argon, 2.5 ml of TFA was put at room temperature, followed by stirring for 5 minutes. 200 ml of dry $CH_2Cl_2$ was added and then diformylthiophene (0.196 g, 0.9 mmol) was quickly added, followed by stirring at room temperature for 16 hours. Then, triethylamine was slowly added to neutralize the solution, and then DDQ (0.227 g, 1.0 mmol) was added, followed by further stirring for 2 hours. The obtained solution was washed with water, a saturated sodium carbonate aqueous solution and a saturated sodium chloride aqueous solution, then dried over sodium sulfate and concentrated. The obtained crude crystals were treated by column chromatography and then purified by recrystallization ($CH_2Cl_2$/MeOH) to obtain dithiaporphyrin 5 as the desired product in a yield of 37%. Appearance: greenish brown solid (containing steric isomers), mp: >130° C. (decomposed). The elemental analysis, NMR and measurement of mass spectrum, were carried out to confirm the desired product.

PREPARATION EXAMPLE 4

Preparation of 21-thiaporphyrin

In the same manner as in Preparation Example 3, thiatripyran dicarboxylic acid 4 was prepared. In the same manner as in Preparation Example 3 except that this thiatripyran dicarboxylic acid 4 and a pyrrole derivative instead of thiophene were employed, a thiaporphyrin compound having the following bicyclo structure was prepared by the following synthesis route.

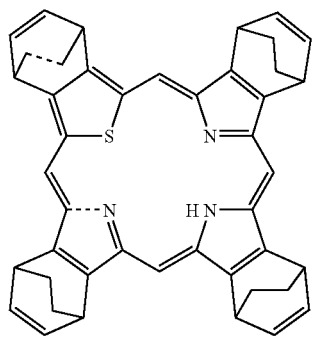

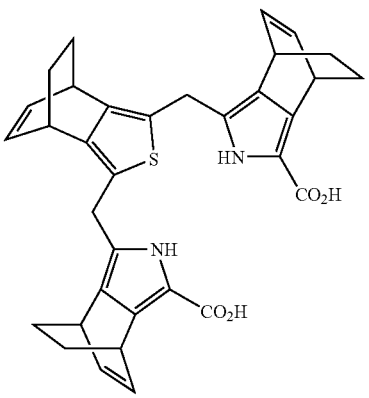

4

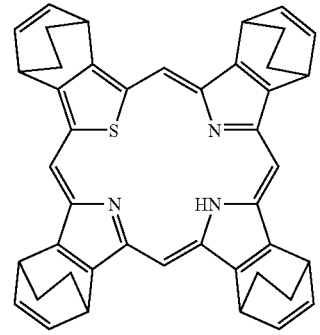

6

Into a light-shielded 500 ml flask, thiatripyran dicarboxylic acid 4 (0.508 g, 0.9 mmol) was put, and after flushing the interior with argon, 2.5 ml of TFA was put at room temperature, followed by stirring for 5 minutes. 200 ml of dry $CH_2Cl_2$ was added, and then, diformylpyrrole (0.181 g, 0.9 mmol) was quickly added, followed by stirring at room temperature for 16 hours. Then, triethylamine was slowly added to neutralize the solution, and then DDQ (0.227 g, 1.0 mmol) was added, followed by stirring for further 2 hours. The obtained solution was washed with water, a saturated sodium carbonate aqueous solution and a saturated sodium chloride aqueous solution, then dried over sodium sulfate and concentrated. The crude crystals were treated by column chromatography (alumina, 50% ethyl acetate/hexane) and then purified by recrystallization ($CH_2Cl_2$/MeOH) to obtain thiaporphyrin 6 as the desired product in a yield of 42%. Appearance: greenish purple solid (containing steric isomers), mp: >130° C. (decomposed). The elemental analysis, NMR and measurement of mass spectrum, were carried out to confirm the desired product.

EXAMPLE 1

On a N-type silicon substrate (Sb-doped, resistivity: at most 0.02 Ωcm, manufactured by Sumitomo Metals Industries, Ltd.) having 300 nm of an oxide film formed thereon, gold electrodes (source and drain electrodes) having a length (L) of from 2.5 to 50 µM, a widthL (W) of 250 µm or a gap of 1,000 µm, were formed by photolithography. Further, the oxide film at a position different from these electrodes, was etched with a hydrofluoric acid/ammonium fluoride solution, and to the exposed Si portion, gold was vapor-deposited to form an electrode (gate electrode) to apply a voltage to the silicon substrate.

2 mg of the bicyclo compound (I) obtained in Preparation Example 1 was dissolved in 1 ml of chloroform, and this solution was dropped between the source and drain electrodes, followed by evaporation of the solvent, and this operation was repeated a few times to obtain a good film. The X-ray diffraction of this film was observed, whereby no sharp peak was observed. Further, this film was observed under a crossed nicols microscope, whereby a dark image over the entire surface was obtained, thus indicating an isotropic film. Accordingly, the obtained film was found to be amorphous.

This substrate was heated at 210° C. for 10 minutes. The X-ray diffraction of the obtained film was observed, whereby a sharp peak was observed. Further, the film was observed under a crossed nicols microscope, whereby a colored domain structure was observed. Accordingly, the obtained film was found to be crystalline. This indicates that the bicyclo compound changed to tetrabenzoporphyrin and became crystalline. Further, the obtained film had a low solubility in a solvent and was hardly soluble in an organic solvent.

Figure 8:
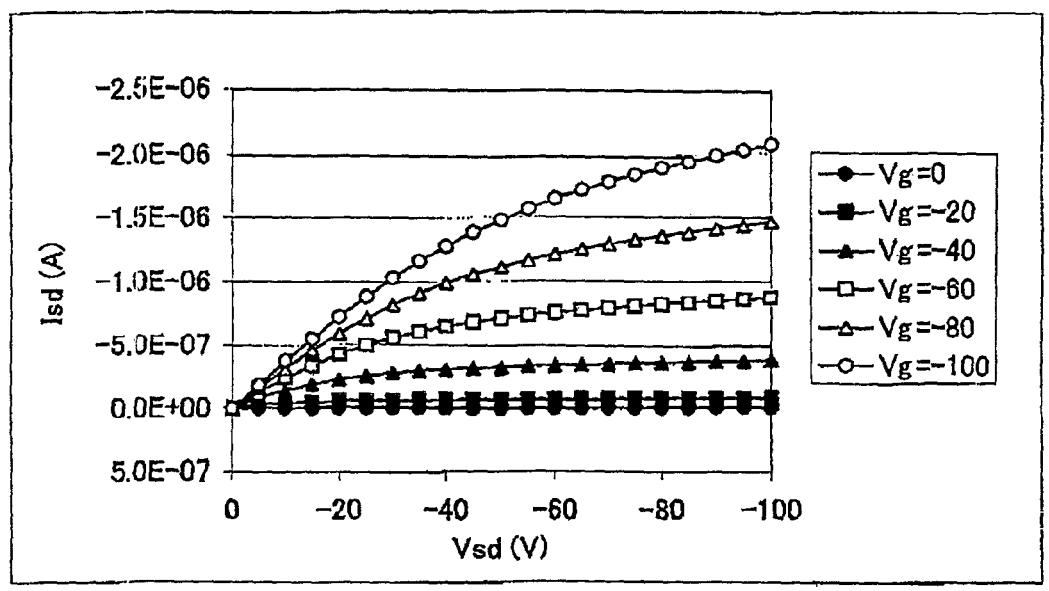
FIG. 8 is a graph showing the results of the observation of the FET characteristics in Example 1.

The characteristics of the field effect transistor thus obtained were measured by means of a semiconductor parameter analyzer 4155C manufactured by Agilent Technologies. The results of the measurement are shown in FIG. 8.

The operation may be represented as follows, wherein Id is the current flowing under a voltage Vd applied across the source and the drain, Vg is the voltage applied to the source and the gate, Vt is the threshold voltage, Ci is the capacitance per unit area of the insulating film, L is the distance between the source electrode and the drain electrode, W is the width, and µ is the mobility of the semiconductor layer.

When Vd<Vg−Vt, $$I_d = \mu C_i (W/L)[(V_s - V_t)V_d - (V_d^2/2)]$$

when Vd>Vg, $$I_d = (1/2)\mu C_i (W/L)(V_s - V_t)^2$$

Thus, the mobility µ is an important parameter of the material governing the characteristics of the device (transistor), and in order to obtain a device having high characteristics, a material having high µ is required.

Inversely, µ can be obtained from the current-voltage characteristics of the device. To obtain µ, the formula (1) or (2) is employed. However, for the mobility µ, there are a few definitions, i.e. an effective mobility µeff obtained from the slope of Id–Vd at a certain Vg, a field effect mobility µFE obtained from the slope of Id–Vg at a certain Vd, and a saturated mobility µsat obtained from the slope of $Id^{1/2}$–Vg of the saturated current portion of the formula (2). The effective mobility µeff, the field effect mobility µFE and the saturated mobility psat should have the same values in the model obtained by the above formula, and in reality, they become the same value with respect to a semiconductor material whereby ideal FET characteristics can be obtained. However, because of the difference between the real properties of the semiconductor material and the model, they may sometimes take different values.

From FIG. 8, the respective mobilities were obtained, whereby the effective mobility µeff was $1 \times 10^{-3}$ cm$^2$/Vs, the field effect mobility µFE was $1.6 \times 10^{-3}$ cm$^2$/Vs, and the saturated mobility µsat was $0.7 \times 10^{-3}$ cm$^2$/Vs.

EXAMPLE 2

Using chlorobenzene as a solvent, a film of a bicyclo compound was prepared in the same manner as in Example 1 and converted to benzoporphyrin by heating.

The characteristics of the field effect transistor thus obtained were measured by a semiconductor parameter analyzer 4155C, manufactured by Agilent Technologies. The effective mobility µeff was $1.6 \times 10^{-2}$ cm$^2$/Vs, and the saturated mobility µsat was $1.3 \times 10^{-2}$ cm$^2$/Vs.

EXAMPLE 3

On a slide glass having aluminum vapor-deposited thereon, a solution having oxydianiline and benzophenone tetracarboxylic anhydride dissolved in dimethylformamide in a molar ratio of 1:1, was spin-coated and heat-treated at 250° C. to prepare a polyimide film having a thickness of 500 nm. On this film, a film of a bicyclo compound was formed in the same manner as in Example 1 and converted to benzoporphyrin by heating.

Gold was vapor-deposited thereon through a shadow mask prepared by employing a tungsten wire having a diameter of 25 µm at the gap portion, to prepare source and drain electrodes having a gap having a width (W) of 250 µm and a length (L) of 25 µm. The characteristics of the field effect transistor thus obtained, were measured by a semiconductor parameter analyzer 4155C, manufactured by Agilent Technologies. The effective mobility µeff was $3.7 \times 10^{-2}$ cm$^2$/Vs, and the saturated mobility µsat was $1.4 \times 10^{-2}$ cm$^2$/Vs.

EXAMPLE 4

Using a zinc complex prepared in Preparation Example 4, FET was prepared in the same manner as in Example 1. The characteristics of this FET were measured, whereby the effective mobility µeff was $1.9 \times 10^{-4}$ cm$^2$/Vs, and the saturated mobility µsat was $1.3 \times 10^{-4}$ cm$^2$/Vs.

EXAMPLE 5

The bicyclo compound (I) obtained in Preparation Example 1 was heated at 210° C. for 30 minutes and converted to tetrabenzoporphyrin. This product was vacuum vapor-deposited on the same electrode substrate as in Example 1 under a vacuum degree of $2 \times 10^{-6}$ Torr ($2.6 \times 10^{-3}$ Pa) to prepare a field effect transistor. The relation between the substrate temperature during vacuum deposition and the mobility (the saturated mobility) of transistor is shown in Table 1. From this relation, it is evident that the mobility differs depending upon the substrate temperature.

TABLE 1

| Substrate temperature | Saturated mobility μsat |
|---|---|
| Room temperature | $2.9 \times 10^{-4}$ cm$^2$/Vs |
| 80° C. | $2.3 \times 10^{-6}$ cm$^2$/Vs |
| 150° C. | $5.6 \times 10^{-7}$ cm$^2$/Vs |
| 200° C. | $2.8 \times 10^{-8}$ cm$^2$/Vs |

Figure 9:
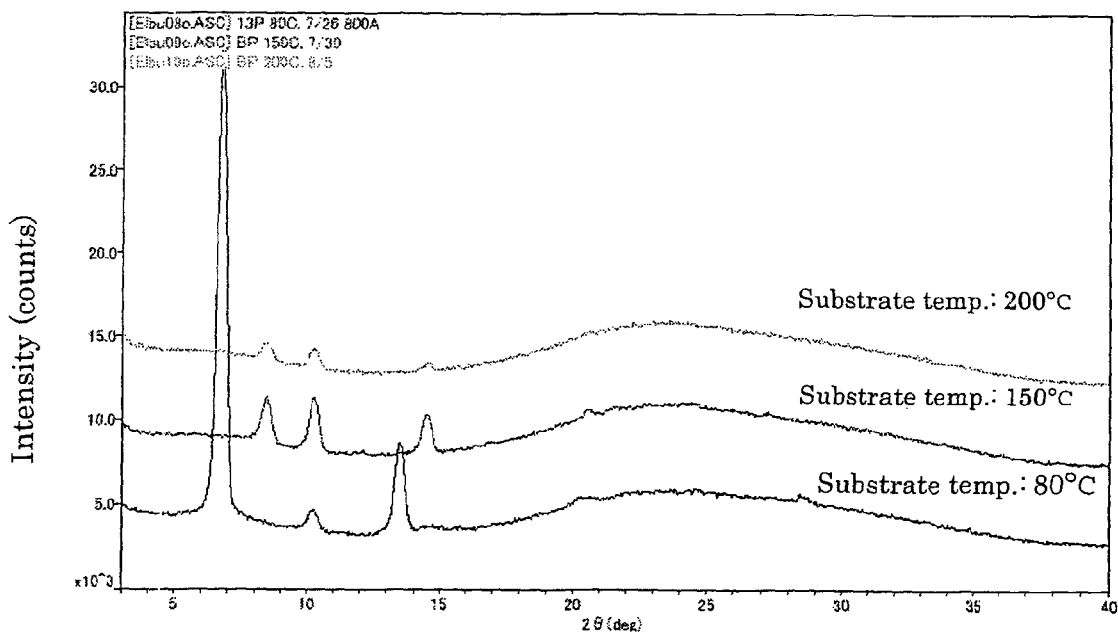
FIG. 9 is a graph showing the X-ray diffraction patterns of the semiconductor film in Example 5.

Further, in FIG. 9, with respect to ones vapor-deposited at a temperatures of 80° C. to 200° C., the X-ray diffraction patterns are shown. From the comparison of these, it is considered that crystal forms are different as between at least 150° C. and at most 80° C., and in either case, the peak is little, and it is thus considered that the film is strongly aligned to the substrate. Accordingly, it is considered that there was a substantial difference in the observed mobility.

EXAMPLE 6

The benzoporphyrin of Preparation Example 1 was subjected to chloroform/silica gel column chromatography and chloroform/methanol recrystallization repeatedly to obtain a highly purified product. In Preparation Example 1, the purity at an absorbance at 254 nm by liquid chromatography was 99.0%, whereas with this highly purified product, it was 99.7%.

A field effect transistor was prepared in the same manner as in Example 1 except that using this highly purified product, a precursor film was prepared by spin coating in a dry nitrogen and heated at 210° C. for 5 minutes in nitrogen on a hot plate.

For evaluation, a saturated mobility μsat to be calculated from the plotted inclination of the gate voltage and the square route of the drain current Id, was obtained based on the relation between the gate voltage and the current in the saturated region, whereby the saturated mobility μsat was found to be at least 0.016 cm$^2$/Vs. Further, the ON/OFF ratio was obtained from the ratio of the drain current between in the case of a gate voltage of 0 V and in the case of a gate voltage of −30 V, at a drain voltage of −30 V, whereby the ON/OFF ratio was found to be at least $10^3$, and $10^5$ at best.

Figure 10:
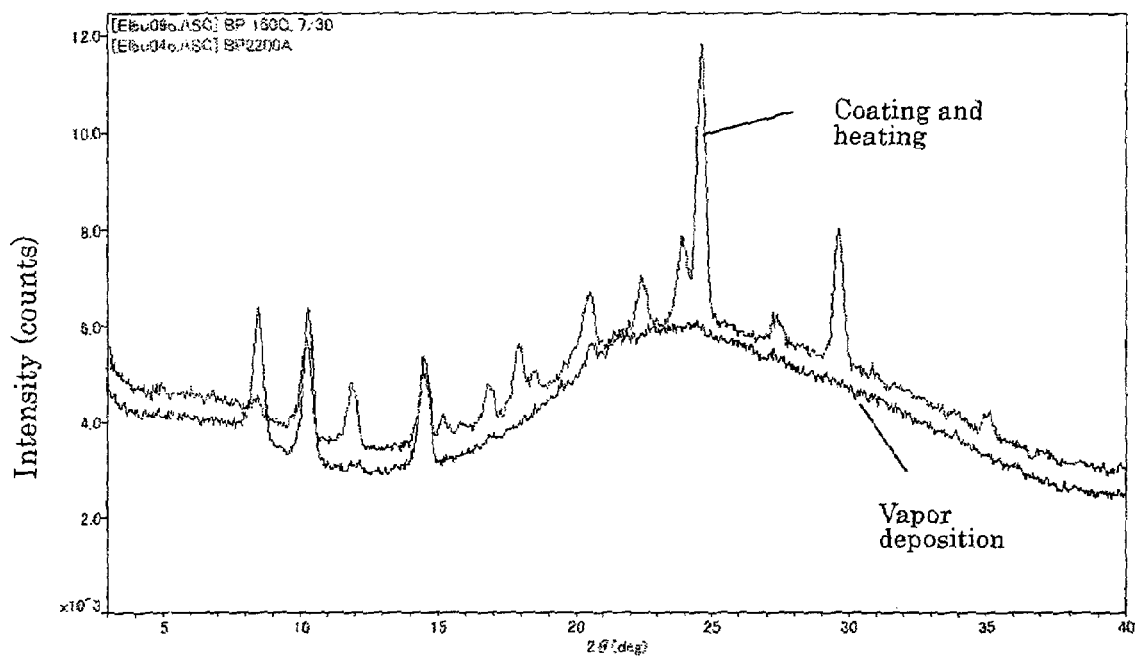
FIG. 10 is a graph showing the X-ray diffraction patterns of the semiconductor films in Examples 5 and 6.

FIG. 10 shows the X-ray diffraction patterns of a semiconductor layer obtained in Example 6 and a semiconductor layer prepared by vapor deposition at a substrate temperature of 150° C. in Example 5. The peaks at low angles agree to each other, whereby both appear to be similar crystals, but the diffraction patterns are substantially different. Therefore, the states of the films such as the alignment, crystallinity, etc. are considered to be different. Accordingly, it is considered that the semiconductor layer obtained by coating and heating exhibits excellent characteristics.

EXAMPLE 7

On the device prepared in Example 6, a toluene solution of polymethyl methacrylate (PMMA) was spin-coated, followed by drying at 120° C. to form a film of 2 μm.

Figure 11:
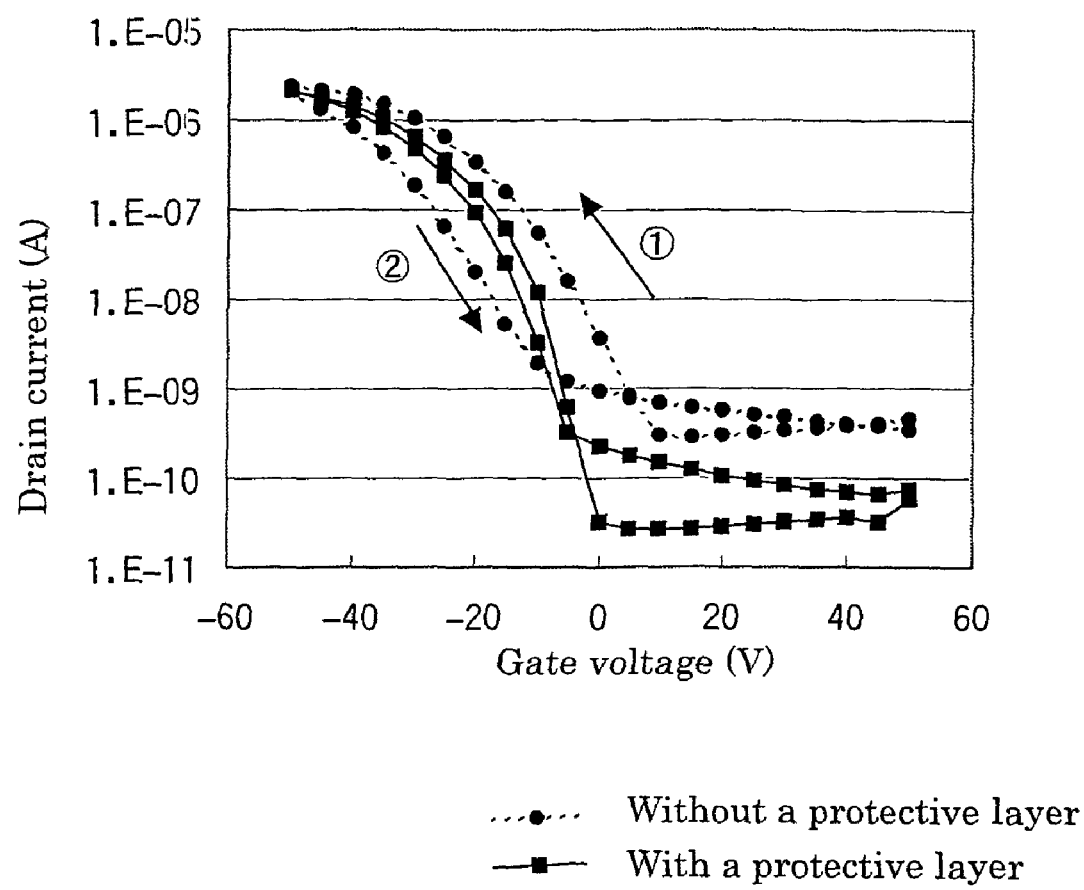
FIG. 11 is a graph showing the hysteresis of the drain current by scanning of the gate voltage, of the devices of Examples 6 and 7.

To this device, and to the device prepared in Example 6, while fixing the drain voltage at −30 V, the gate voltage was changed from 50 V→50 V→50 V, and the drain current was measured. The results are shown in FIG. 11. It is evident that even in the absence of the PMMA film, the ON/OFF ratio is at least $10^3$ and thus shows good characteristics, but if the PMMA film is provided, the hysteresis of the drain current by scanning of the gate voltage is small, and also the ON/OFF ratio is improved.

EXAMPLE 8

A FET was prepared in the same manner as in Example 1 by employing the dithiaporphyrin prepared in Preparation Example 3. Namely, on a substrate having electrodes formed in the same manner as in Example 1, a precursor having the following bicyclo structure was coated and then heat-treated to prepare a film of tetrabenzodithiaporphyrin. The electrical characteristics of the FET device thus obtained were measured, whereby the FET characteristics were observed, and the saturated mobility was $1.1 \times 10^{-4}$ cm$^2$/Vs, and the ON/OFF ratio was 1,000.

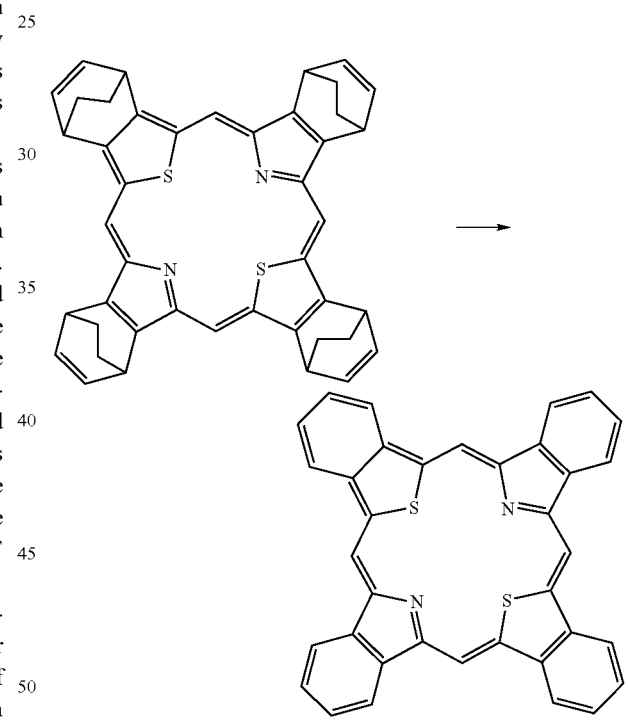

EXAMPLE 9

A FET was prepared in the same manner as in Example 1 by employing the thiaporphyrin prepared in Preparation Example 4. Namely, on a substrate having electrodes formed in the same manner as in Example 1, the precursor having the following bicyclo structure was coated and then heat-treated to prepare a film of tetrabenzothiaporphyrin. The electrical characteristics of the FET device thus obtained were measured, whereby the FET characteristics were observed, and the saturated mobility was $2.5 \times 10^{-5}$ cm$^2$/Vs, and the ON/OFF ratio was 380.

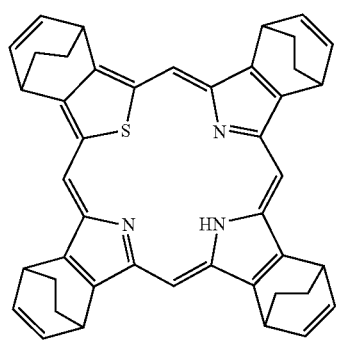

→

EXAMPLE 10

A FET was prepared in the same manner as in Example 1 by employing the following zinc complex. Namely, on a substrate having electrodes formed in the same manner as in Example 1, a precursor having the following bicyclo structure was coated and then heat-treated to prepare a semiconductor film, whereby a field effect transistor was obtained. The electrical characteristics of the FET device thus obtained were measured, whereby the saturated mobility μsat was $0.7 \times 10^{-4}$ cm²/Vs, and the effective mobility μeff was $1 \times 10^{-4}$ cm²/Vs.

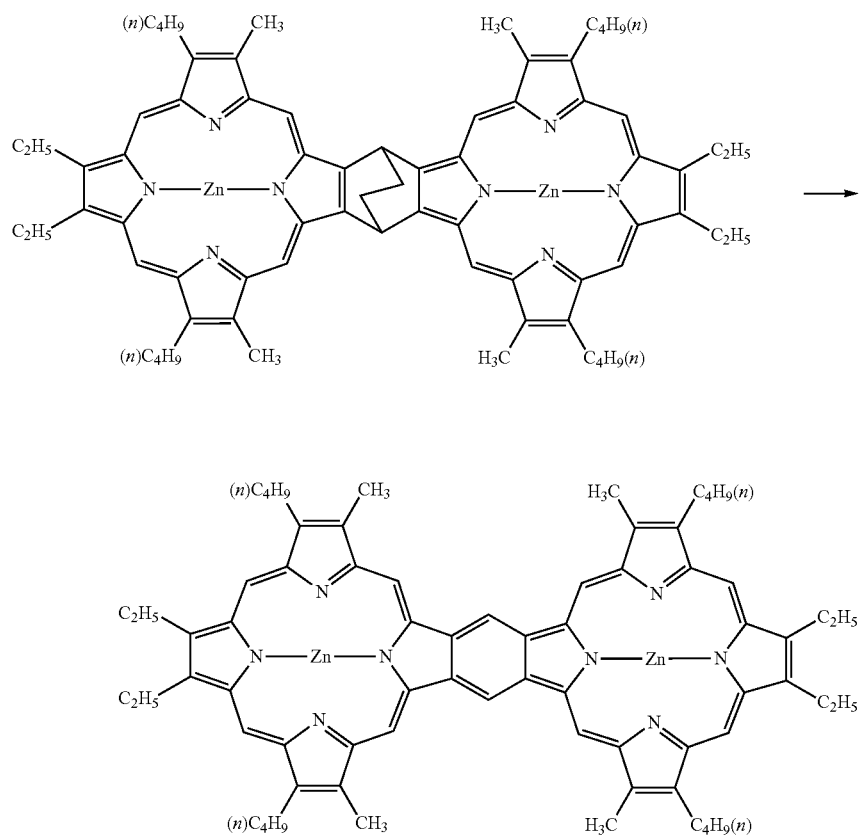

-continued

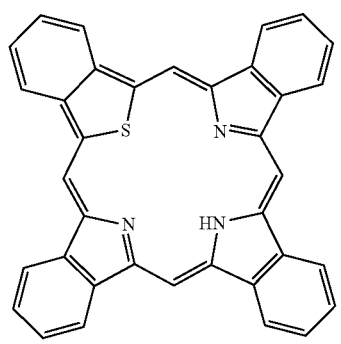

COMPARATIVE EXAMPLE 1

Fields effect transistors were prepared by employing the generalized porphyrin compounds represented by the following respective formulas, and their electrical characteristics were evaluated, but in each case, no FET characteristics were observed.

The molecular structures of these generalized porphyrin compounds were obtained by e.g. the molecular orbital method (such as MOPAC) and the molecular dynamics method (MM2), whereby it was confirmed that atoms constituting the porphyrin skeleton are present at positions apart at least 1 Å from the generalized porphyrin ring plane.

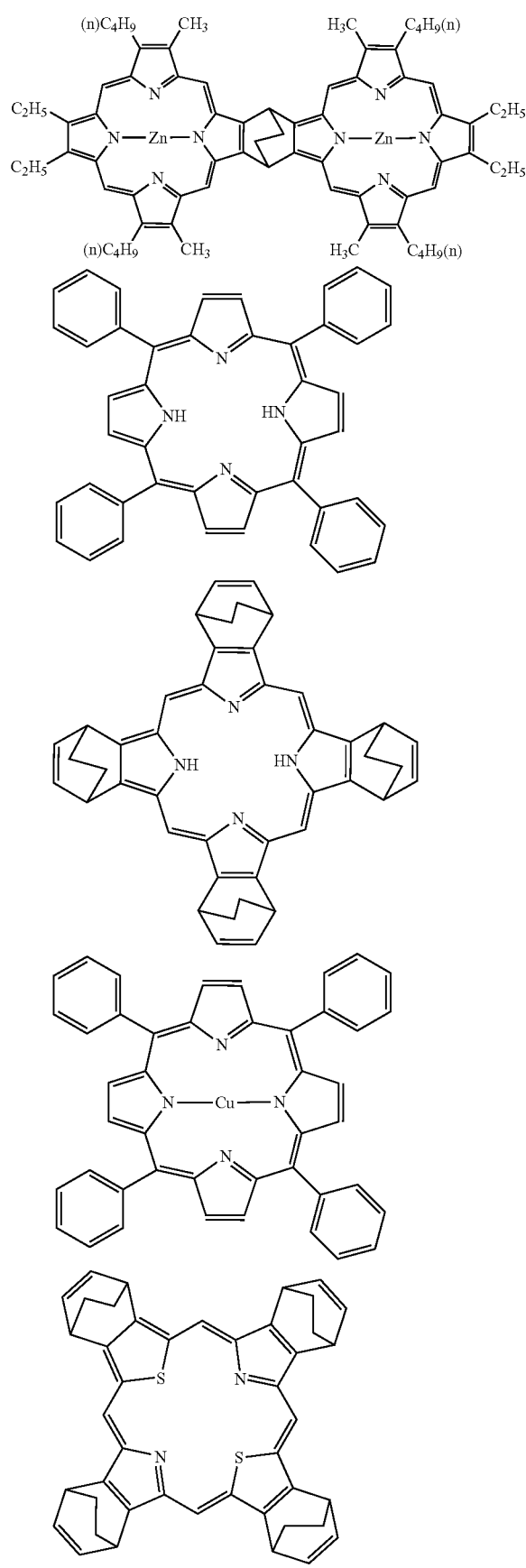
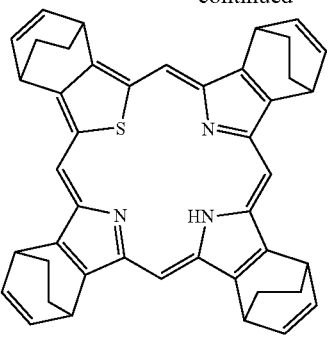

According to the present invention, an organic semiconductor material is used for an organic electronic device, whereby it can be produced by a relatively low temperature process, whereby a plastic film can be used as the substrate, and it is possible to prepare a device which is light in weight, excellent in flexibility and scarcely breakable. Accordingly, a field effect transistor with a thin film having flexibility, can be prepared, and this can be utilized for a switching element for each cell, whereby a flexible active matrix liquid crystal display can be prepared, and thus it is widely applicable.

Further, an organic semiconductor material and an organic electronic device containing the generalized porphyrin compound of the present invention, has a high carrier mobility and stability, and further can be prepared by a simple production process. Further, the field effect transistor of the present invention has a little leak current and a large ON/OFF ratio and thus has a merit such that the stability of the film and characteristics is high and the useful life is long. Further, the useful temperature range is wide, the film forming property is good, it is applicable to a large area, and it can be prepared at low cost.

What is claimed is:

1. A method for producing an organic electronic device comprising a semiconductor layer comprising a generalized porphyrin compound, a protective layer formed directly or via another layer on the semiconductor layer, an insulating layer containing a polymer, and at least two electrodes, which method comprises producing the semiconductor layer by converting a precursor in the form of a film of the precursor by a coating process and then converting the precursor by change of its chemical structure to form the semiconductor layer, wherein said generalized porphyrin compound is a compound which has a porphyrin skeleton and which has a molecular structure such that the distance from the porphyrin ring plane to the center of each atom forming the porphyrin skeleton, is not more than 1 Å.

2. The method according to claim 1, wherein the conversion is conducted by heating.

3. The method according to claim 1, wherein the generalized porphyrin compound has a mobility of at least $1 \times 10^{-5}$ cm$^2$/Vs.

4. The method according to claim 1, wherein the generalized porphyrin compound has a molecular weight of at most 2,000.

5. The method according to claim 1, wherein the generalized porphyrin compound is a benzoporphyrin.

6. The method according to claim 1, wherein the generalized porphyrin compound contains no metal.

7. The method according to claim 1, wherein the generalized porphyrin compound contains copper.

8. The method according to claim 1, wherein the organic electronic device comprises the semiconductor layer, an insulating layer, a source electrode, a drain electrode and one gate electrode as the sole gate electrode.

* * * * *